US006836559B2

(12) United States Patent
Abdel-Fattah et al.

(10) Patent No.: US 6,836,559 B2
(45) Date of Patent: Dec. 28, 2004

(54) AUTOMATED VIDEO-MICROSCOPIC IMAGING AND DATA ACQUISITION SYSTEM FOR COLLOID DEPOSITION MEASUREMENTS

(75) Inventors: Amr I. Abdel-Fattah, Albuquerque, NM (US); Paul W. Reimus, Los Alamos, NM (US)

(73) Assignee: The Regents of the University of California, Oakland, CA (US)

( * ) Notice: Subject to any disclaimer, the term of this patent is extended or adjusted under 35 U.S.C. 154(b) by 512 days.

(21) Appl. No.: 09/802,489

(22) Filed: Mar. 9, 2001

(65) Prior Publication Data

US 2004/0218798 A1 Nov. 4, 2004

Related U.S. Application Data

(60) Provisional application No. 60/188,933, filed on Mar. 9, 2000.

(51) Int. Cl.[7] .................................................. G06K 9/00
(52) U.S. Cl. ........................ 382/134; 382/321; 382/294; 377/10; 600/156
(58) Field of Search ............................... 382/133, 134, 382/128, 129, 321, 294; 377/10; 702/26; 324/71.2; 356/39; 378/43; 359/227, 228, 368; 600/156, 160; 128/922

(56) References Cited

U.S. PATENT DOCUMENTS

| | | | |
|---|---|---|---|
| 3,937,066 A | | 2/1976 | Green et al. |
| 4,154,669 A | | 5/1979 | Goetz |
| 4,752,567 A | | 6/1988 | De Brabander et al. |
| 4,975,863 A | * | 12/1990 | Sistler et al. ............... 382/110 |
| 4,992,659 A | * | 2/1991 | Abraham et al. ........... 250/306 |
| 5,254,857 A | | 10/1993 | Ross et al. |
| 5,330,911 A | | 7/1994 | Hubbell et al. |
| 5,496,999 A | | 3/1996 | Linker et al. |
| 5,673,338 A | | 9/1997 | Denenberg et al. |
| 5,717,778 A | * | 2/1998 | Chu et al. ................... 382/133 |
| 5,932,872 A | | 8/1999 | Price |
| 5,968,731 A | | 10/1999 | Layne et al. |
| 6,280,960 B1 | * | 8/2001 | Carr ........................... 435/7.2 |
| 6,330,349 B1 | * | 12/2001 | Hays et al. ................. 382/128 |
| 2002/0011266 A1 | * | 1/2002 | Garver et al. ................ 137/93 |

OTHER PUBLICATIONS

Weiss, Michael; Luthi, Yves; Ricka, Jaro; Jorg, Thomas; and Bebie, Hans; Colloidal Particles At Solid–Liquid Interfaces: Mechanisms of Desorption Kinetics, Journal of Colloid and Interface Science, vol. 206, pp 322–31, (1998).

(List continued on next page.)

Primary Examiner—Bhavesh M. Mehta
Assistant Examiner—Barry Choobin
(74) Attorney, Agent, or Firm—John P. O'Banion

(57) ABSTRACT

A video microscopic visualization system and image processing and data extraction and processing method for in situ detailed quantification of the deposition of sub-micrometer particles onto an arbitrary surface and determination of their concentration across the bulk suspension. The extracted data includes (a) surface concentration and flux of deposited, attached and detached colloids, (b) surface concentration and flux of arriving and departing colloids, (c) distribution of colloids in the bulk suspension in the direction perpendicular to the deposition surface, and (d) spatial and temporal distributions of deposited colloids.

52 Claims, 20 Drawing Sheets

OTHER PUBLICATIONS

Luthi, Yves; and Ricka, Jaro; "Colloidal Particles at Water–Glas Interface: Analyzing Videomicroscopic Data," Journal of Colloid and Interface Science, vol. 206, pp 203–313, (1998).

Luthi, Yves; Ricka, Jaro; and Borkovec, Michal; "Colloidal Particles at Water–Glass Interface Deposition Kinetics and Surface Heterogeneity," Journal of Colloid and Interface Scince, vol. 206, pp 314–321, (1998).

Screen Shots from http://www.defimg.com/MSQ.htm, "Complete Image Analysis System," 3 pages, Mar. 6, 2001.

Screen Shots from http://www.beckmancoulter.com/coulter/pc/ss000099.asp, "Coulter Delsa 440 SX," 2 pages, Mar. 6, 2001.

Screen Shots from http://www.beckmancoulter.com/coulter/pc/ss000095.asp, Coulter Counter Multisizer 3, 3 pages, Mar. 6, 2001.

* cited by examiner

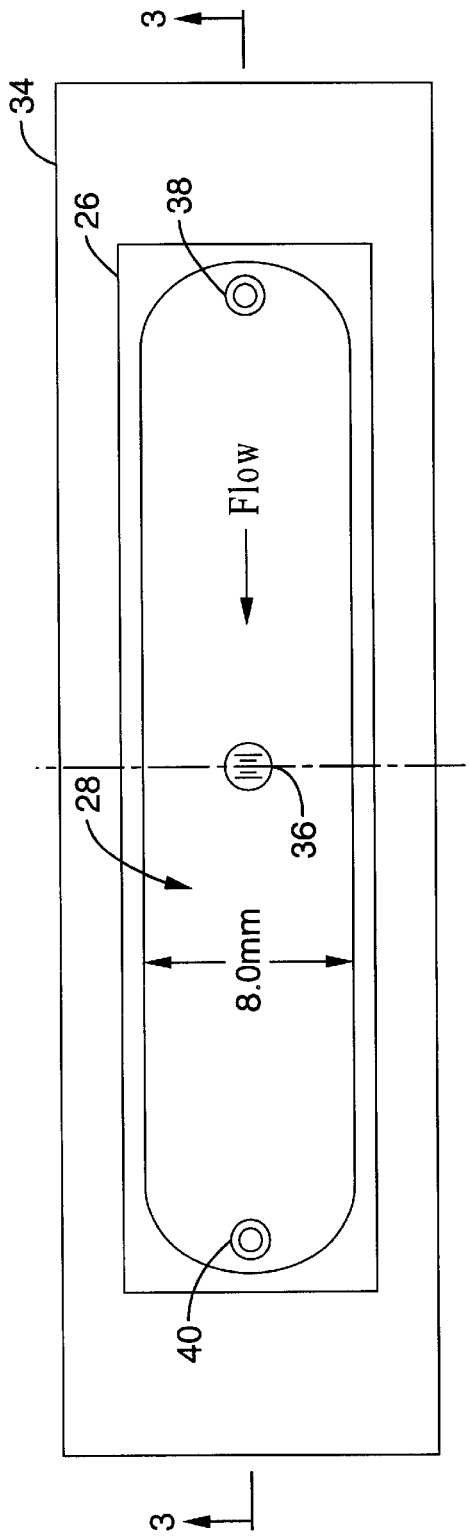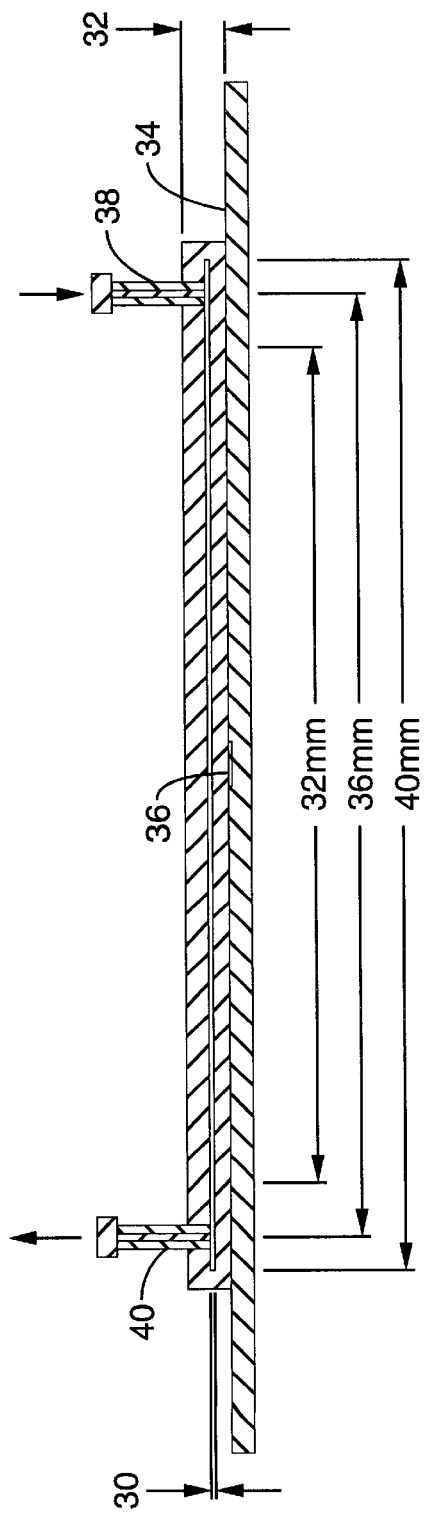

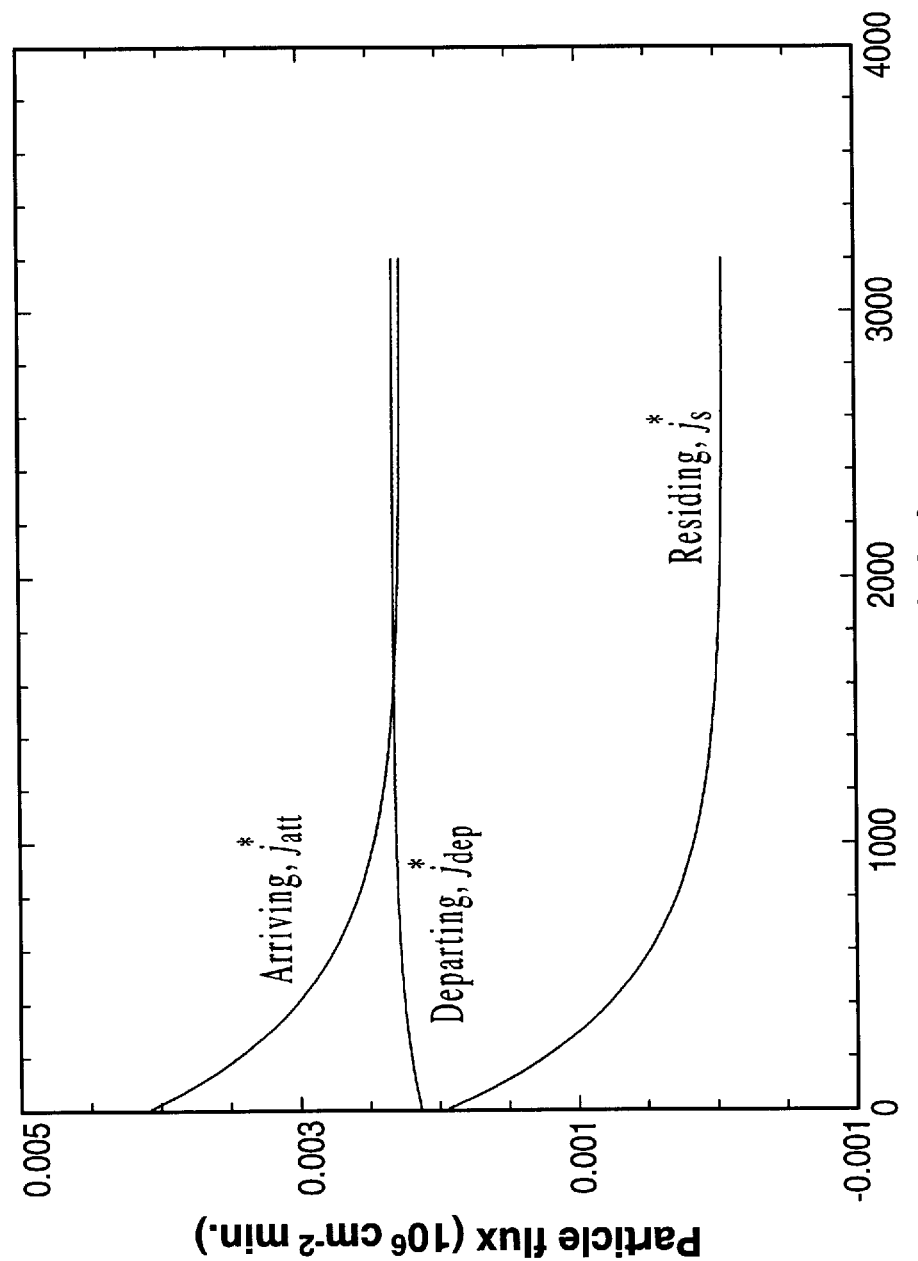

AUTOMATED VIDEO-MICROSCOPIC IMAGING AND DATA ACQUISITION SYSTEM FOR COLLOID DEPOSITION MEASUREMENTS

CROSS-REFERENCE TO RELATED APPLICATIONS

The application claims priority from U.S. provisional application Ser. No. 60/188,933 filed on Mar. 9, 2000, incorporated herein by reference.

STATEMENT REGARDING FEDERALLY SPONSORED RESEARCH OR DEVELOPMENT

This invention was made with Government support under Grant No. W-7405-ENG-36, awarded by the Department of Energy. The Government has certain rights in this invention.

REFERENCE TO A MICROFICHE APPENDIX

Not Applicable

BACKGROUND OF THE INVENTION

1. Field of the Invention

This invention pertains generally to automated imaging and data acquisition systems, and more particularly to a table-top system that automatically quantifies the deposition and aggregation kinetics of sub-micrometer- to sub-millimeter-sized particles at an arbitrary surface by simultaneously determining their spatial and temporal distributions at the surface and their diffusion coefficient, velocity, and concentration distributions in the bulk suspension.

2. Description of the Background Art

Colloids are minute particles that are dispersed in different continuous phases. They range from airborne dust and smoke, to foams and emulsions, to proteins and biological cells. Understanding the behavior of these tiny particles is important to research ranging from drug development to environmental remediation. The deposition kinetics of colloids onto different interfaces (e.g., solid/liquid or gas/liquid interfaces) is key to a variety of their applications. For example, in medical drugs, it affects how colloids disperse corrective proteins in body tissue. On the assembly line, it affects how well the paint sprayed onto car bodies will adhere. In the mining industry, it affects how efficiently valuable minerals (like gold) can be separated from waste rock by froth flotation techniques.

Quantifying the deposition kinetics of colloids requires determining their spatial and temporal distribution at a surface (a liquid/solid or gas/liquid interface); determining the position of each colloid when it arrives at, attaches to, and detaches from that surface; and determining the average concentration (or flux) of colliding, attaching, and detaching particles. The large number of particles (typically thousands) that must be tracked and the time-dependence and randomness of their movements rule out quantifying them by manual means.

Experimental methods used to study colloid deposition in different geometries can be classified into either direct or indirect methods. Indirect methods measure quantities that are unequivocally related to the number of deposited colloids. Examples include: (a) the depletion method, in which the change in the number of colloids in the bulk suspension is measured over time and correlated to the average number of deposited colloids, (b) the packed-bed column method, in which the capture of colloids by the packed-bed of a well-defined granular material is determined, by measuring the difference between the inlet and outlet colloid bulk concentrations, and related to the number of deposited colloids onto the surfaces of the granular material, (c) the light scattering method, in which the intensity of light scattering by deposited colloids, in the direction normal to the incident light beam, is measured and related to the number of deposited colloids, and (d) the radioactive tracer method, in which the radiation emitted by deposited colloids tagged with a suitable $\gamma$-ray-emitting material is measured and related to their surface concentration.

An inherent limitation to all indirect methods is the inability to quantify the attachment and detachment events of the colloids during the deposition process or their spatial and temporal distribution on the surface. The first two methods (a and b) are also labor intensive and subject to human errors in measuring the changes in the bulk concentration of the colloids. Those changes are typically measured by manually sampling and measuring using, for example, the Coulter principle or light obscuration methods. Moreover, these two methods implicitly assume that the colloid deposition onto the surface is uniform and that the number of deposited colloids equals those lost from the bulk suspension. Thus colloids removed from the bulk suspension by processes other than deposition (e.g., mechanical filtration, coagulation) or by deposition in the sampling tubes are not accounted for, which can potentially skew the experimental results. The last two methods (b and c) are also subject to counting errors due to the background light scattering or radioactivity. Neither method can distinguish between mobile colloids close to the surface and colloids deposited onto the surface.

These limitations of indirect methods have precluded their use in studies aiming at gaining a quantitative understanding of the underlying processes or validating colloid deposition theories or models. Detailed information on the deposition of colloids, larger than ~0.3–0.5 $\mu$m, can be obtained in situ using direct visualization and appropriate image processing methods. These methods can track the time when and the position where each particle attaches to and detaches from the surface, thus the temporal and spatial distributions of the particles at the surface. Direct in situ video microscopic techniques have been successfully employed to investigate colloid deposition at the stagnation point, and in parallel-plate channels. These investigations have demonstrated that direct methods are capable of providing important information beyond the capabilities of indirect methods.

Almost all experiments reported on colloid deposition in parallel-plate geometry have employed in situ direct video microscopic techniques. For example, phase-contrast light microscopy has been used in conjunction with an image processing and data extraction routine to investigate the deposition of 736 nm and 830 nm polystyrene colloids from a flowing suspension through a 0.06 cm aperture parallel-plate channel onto glass and plastic substrates. However, because that system has a relatively low spatial optical resolution, an ultralong working distance objective lens with a relatively high magnification is used, reducing the field of view to only ~$1.7 \times 10^{-4}$ cm$^2$, and hence decreasing the statistical accuracy of the measurements. Further, the image processing and data extraction routine used could not establish full connectivity between deposited colloids in successive images. Also, the number of attached and detached colloids at the surface was determined by labeling the colloids with different gray-scale values. The 8-bit gray-scale used therewith indicates that the number of labeled colloids is limited to a total of 256, thus the data extraction ceased once the total number of attachment or detachment events reaches 256.

The evanescent field technique has also been utilized in conjunction with an elaborate data extraction routine to quantify the deposition of 310-nm diameter fluorescent polystyrene colloids onto the base surface of a rectangular optical glass prism in contact with a flowing colloid suspension in parallel-plate geometry. However, an optical glass prism is necessary to generate the evanescent field at its base surface, which is used as the deposition surface. The underlying parallel-plate channel has an aperture of 0.1 cm. Although it has an optical resolution of ~1 $\mu$m, that system possesses some inherent disadvantages, including: (a) because of the discontinuous illumination of the surface, continuous visualization is hard to achieve, limiting the time resolution between measurements, (b) colloid deposition can only be studied at the base surface of the optical glass prism and the colloids need to be fluorescence-tagged to enhance visualization and image contrast, and (c) the laser beam used to illuminate the deposition surface may induce unfavorable heat and radiation pressure, thus affecting the accuracy of the results.

In summary, the direct in situ methods can separate and accurately quantify the attachment and detachment processes of colloids mingled with their deposition onto a surface. They allow experimentalists to verify measured quantities and immediately detect and correct setup errors during the course of an experiment, avoiding costly reruns. These methods, however, have several limitations such as low spatial resolutions (>1 $\mu$m), limited time resolutions (~2 to 20 minutes), and small fields of view (>0.035 mm$^2$), in addition to being applicable only to colloids larger than ~0.3–0.5 $\mu$m in size. Also, depending on the type of microscopy employed, unavoidable thermal and radiation pressure effects may influence the colloid deposition process. Several uncertainties can also arise from the employed image processing and data extraction methodologies. A major uncertainty in the measurements is caused by the lack of or poor connectivity between colloids in subsequent images. Due to the unavoidable shifting in the view field, a stationary colloid in one image may not correspond to the same colloid in subsequent or preceding images. Another source of uncertainty in the measurements by the direct methods is missing some attachment and detachment events taking place during the "blind" time interval between images. Thus, the measured attachment and detachment concentrations and fluxes may be substantially less than the actual values.

Currently, there is no commercially available technology with the functionality needed to quantify the deposition and aggregation kinetics of minute particles at an arbitrary surface. Software is available, such as the "MSQ Materials Analysis System" (Definitive Imaging, Ltd.), that runs on an Optimas image processor and is designed to be interfaced to visualization hardware. However, MSQ obtains data such as grain size, sphericity, and volume fraction from only non-transient images and cannot quantify attachment/detachment events. Additionally, commercially available instruments are limited in their measurement capabilities and are costly. Examples are the DELSA 440SX (available from Beckman Coulter, Inc.) which measures zeta potential and particle size, and the Multisizer 3 which measures particle size and concentration (also available from Beckman Coulter, Inc.). There are also research instruments that have limited functionality.

Therefore, there is a need for an automated system that offers greater measurement accuracy, simultaneously captures and analyzes information not only on particles deposited at the surface but also on particles moving close to the surface, has a larger field of view so as to provide better statistical data, is suitable for imaging and analyzing submicrometer-sized particles down to ~200-nm-sized particles, can quantify particle deposition onto relatively rough surfaces such as those of rock and metals, has full connectivity, and produces more data for improved measurement accuracy. The present invention satisfies those needs, as well as others, and overcomes deficiencies found in conventional imaging and data acquisition systems.

BRIEF SUMMARY OF THE INVENTION

The present invention comprises a video-microscopic imaging and data acquisition system that makes the study of colloid deposition and aggregation kinetics simple, cost-effective, fast, and consistent. In general terms, the invention visualizes and characterizes colloidal particles that are suspended in or at the surface of a parallel-plate test cell. The colloids appear as bright specks against a dark background. In a typical experiment, the invention acquires, processes, and analyzes over 10,000 images, extracting from them the data needed to fully quantify colloidal deposition kinetics. Typical output data includes (i) the cumulative concentration of colloids attaching to and detaching from the test cell's surface, (ii) the evolution of mobile and immobile colloids at the cell's surface, (iii) and the concentration profile of colloids across the bulk suspension. Key data are extracted and displayed in real time, enabling the user to quickly identify and correct any experimental setup errors.

The present invention enables a person to quantify colloidal processes in real time over periods of up to several days. It combines commercial optical and data-processing equipment with custom software to automatically acquire, store, digitize, process, enhance, and analyze thousands of analog images of colloids at an interface and in suspension. The invention acquires up to thirty images per second and from them extracts the information needed to fully quantify colloidal deposition and to measure the colloids' concentration, diffusion coefficient, and velocity in the suspension. In principle, the invention can also measure their zeta-potential distributions in the bulk suspension.

By way of example, and not of limitation, the invention employs a modified dark-field microscopy to visualize colloidal particles. A suspension of colloids is placed in a parallel-plate test cell approximately 200 micrometers in aperture. The cell is illuminated from below by a 300-watt halogen bulb. Before illuminating the cell, light from the bulb passes through an iris diaphragm and a dry dark-field condenser. The condenser has a numerical aperture of 0.8–0.9, and the iris diaphragm passes only the minimum light intensity needed to illuminate the suspension. Thus only low-numerical-aperture light scattered from the colloids enters the objective lens of a light microscope placed above the test cell.

By adjusting the angle of incident light and correcting for optical aberrations, high contrast from the suspended colloids is achieved even though their size is far below the microscope's resolution limit. The microscope's relatively low magnification (only 20x) produces a large field of view (~0.082 mm$^2$) and offers a reasonable compromise between image resolution and contrast. The colloids appear as bright specks against a dark background (see image), with diffraction making them appear much larger than actual size. A correction cap on the objective lens allows the system to focus on different layers of colloids throughout the suspension. A 3.3x photo eyepiece installed within the microscope's phototube projects the image formed to a charge-coupled device (CCD) camera, whose analog output is then digitized and processed with custom application-specific software. Written in Analytical Language for Images (ALI), the software automates data acquisition, processes and analyzes the sequence of images obtained, and extracts real-time data for graphical display.

The software comprises a main routine and three subroutines. The main routine automates an experiment and applies two algorithms: one captures the kinetics of colloidal deposition onto the surface, and the other determines selected colloidal suspension properties. After processing the acquired images, the main routine extracts the evolution of mobile and immobile colloids at the test cell's upper or lower surface, the cumulative concentration over time of colloids attaching to and detaching from that surface, and the concentration profile of colloids across the suspension. The main routine also saves three sequences of images: one of both mobile and immobile colloids at the surface, one of immobile colloids at the surface, and one of colloids in different layers across the suspension.

The subroutines enable the system to distinguish between colloids that arrive at the surface, collide with it, and attach to it, quantifying the concentration and rate of each set. The subroutines also provide detailed spatial and temporal distribution data on colloids at the surface. When combined, this data allows for quantification of the colloidal deposition process.

The subroutines also solve two major problems encountered in analyzing colloidal deposition data. The first involves determining the concentrations of colloids colliding with and permanently attaching to the surface; the two quantities strongly depend on the time interval between images, $\Delta\tau$. Experiments performed under the same conditions but with different values of $\Delta\tau$ give substantially different results, precluding their comparison. By superimposing images of the surface obtained at different values of $\Delta\tau$, several curves representing the cumulative concentration of attached particles at selected times for each value of $\Delta\tau$ are created. Then by establishing a mathematical relationship between these curves and $\Delta\tau$, two curves that are independent of the time interval are obtained; one for the concentration of colliding particles, and the other for the concentration of attached particles.

The second problem involves establishing "connectivity" between colloid images taken over long periods of time. Connectivity means that a stationary particle in one image corresponds to one, and only one, particle in later images. In accordance with the present invention, connectivity is ensured by choosing a group of stationary particles as a frame of reference for all images and then selecting one of the particles as the reference point to which the coordinates of all other particles are related. If that particle moves in later images, another particle in the original group is selected as a new reference point.

The present invention is ideal for basic and applied research aimed at quantifying the kinetics of sub-micrometer particles deposited onto varied surfaces or aggregated in varied solutions. Used alone, the invention can provide accurate particle concentration data in two ways: (i) by counting the number of particles in different layers across a suspension, which can be done simultaneously while performing a deposition experiment (with ~10% accuracy), or (ii) by using a solution chemistry that allows particles to adhere to the surfaces of the test cell and then counting them at those surfaces. Used in conjunction with an electrophoresis cell, the invention can also be used to study the zeta potential of particles by automatically determining the particles' mobility in the direction normal to an applied electric field. The zeta potential of particles dispersed in aqueous media is an important characteristic that determines their electrostatic interaction with each other and with substrate materials.

An object of the invention is to obtain particle arrival and deposition concentrations independent of the experiment design.

Another object of the invention is to capture both particles immobilized at the surface and those moving close to it, and distinguishes between them, without refocusing.

Another object of the invention is to obtain particle concentration, diffusion coefficient, and velocity across the test cell during deposition or aggregation experiments.

Another object of the invention is to capture, process, and analyze over 10,000 images during the course of a typical experiment.

Another object of the invention is to provide a system wherein users can interact with the system remotely through the Internet and can share real-time data with others during the course of an experiment.

Another object of the invention is to extract and display key data on-line, enabling users to quickly identify and correct any experimental setup errors.

Another object of the invention is to establish connectivity over time periods on the order of days, reducing significant errors that result when connectivity is lacking.

Another object of the invention is to use standard light as an illumination source, which eliminates the thermal effects that can be induced by lasers, reduces equipment and operating costs, and suits the system to biological studies.

Another object of the invention is to provide an imaging system with a wide field of view.

Another object of the invention is to use various materials as the substrate for particle deposition (e.g., thin sections of natural rocks or metals as well as gas/liquid interfaces).

Another object of the invention is to visualize particles at varied depths in a suspension without deterioration so that those particles are analyzed and quantified with the same accuracy as surface particles.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 2 is a top plan view of a parallel-plate test cell for use with the system shown in FIG. 1.

FIG. 3 is a cross-sectional view of the parallel-plate test cell of FIG. 2 taken through line 3—3.

FIG. 23 is a graph showing colloid flux values as a function of time.

DETAILED DESCRIPTION OF THE INVENTION

For illustrative purposes the present invention is embodied in the apparatus and method generally shown in, and described with reference to, FIG. 1 through FIG. 23. It will be appreciated that the apparatus may vary as to configuration and as to details of the parts, and that the method may vary as to the specific steps and sequence, without departing from the basic concepts as disclosed herein.

1. Definitions

Deposited colloids: colloids found immobile at the surface at a given time, t, during the experiment.

Attached colloids: all colloids that have ever attached to the surface up until time t for a finite period of time≧the time interval between images, $\Delta\tau$.

Detached colloids: all colloids that have ever detached from the surface up until time t after a finite period of time>the time interval between images, $\Delta\tau$.

Arrived colloids: all colloids that have ever attached to the surface up until time t for a period of time≧0, i.e., all colloids that have collided with the surface up until time t.

Departed colloids: all colloids that have ever detached from the surface up until time t after a period of time>0.

Surface concentration of deposited colloids, $N_s(t)$: the number of colloids deposited within a finite area, S, of the surface at any given time t.

Colloid deposition flux, $j_s(t)$: the rate at which colloids deposit onto the surface area S, i.e., the rate by which $N_s(t)$ changes with respect to time.

Surface concentration of attached colloids, $N_{att}(t)$: the number of all colloids that have ever attached to the surface area S up until time t for a finite period of time≧$\Delta\tau$.

Colloid attachment flux, $j_{att}(t)$: the rate at which colloids attach to the surface area S, i.e., the rate by which $N_{att}(t)$ changes with respect to time.

Surface concentration of detached colloids, $N_{det}(t)$: the number of all colloids that have ever detached from the surface area S up until time t after a finite period of time≧$\Delta\tau$.

Colloid detachment flux, $j_{det}(t)$: the rate at which colloids detach from the surface area S, i.e., the rate by which $N_{det}(t)$ changes with respect to time.

Surface concentration of arrived colloids (actual surface concentration of attached colloids), $N_{att}(t)$: the number of all colloids that have ever attached to the surface area S up until time t for a finite period of time≧0.

Colloid attachment flux, $j_{att}(t)$: the rate at which colloids attach to the surface area S, i.e., the rate by which $N_{att}(t)$ changes with respect to time.

Surface concentration of detached colloids, $N_{det}(t)$: the number of all colloids that have ever detached from the surface area S up until time t after a finite period of time≧$\Delta\tau$.

Colloid detachment flux, $j_{det}(t)$: the rate at which colloids detach from the surface area S, i.e., the rate by which $N_{det}(t)$ changes with respect to time.

2. System Configuration

Figure 1:
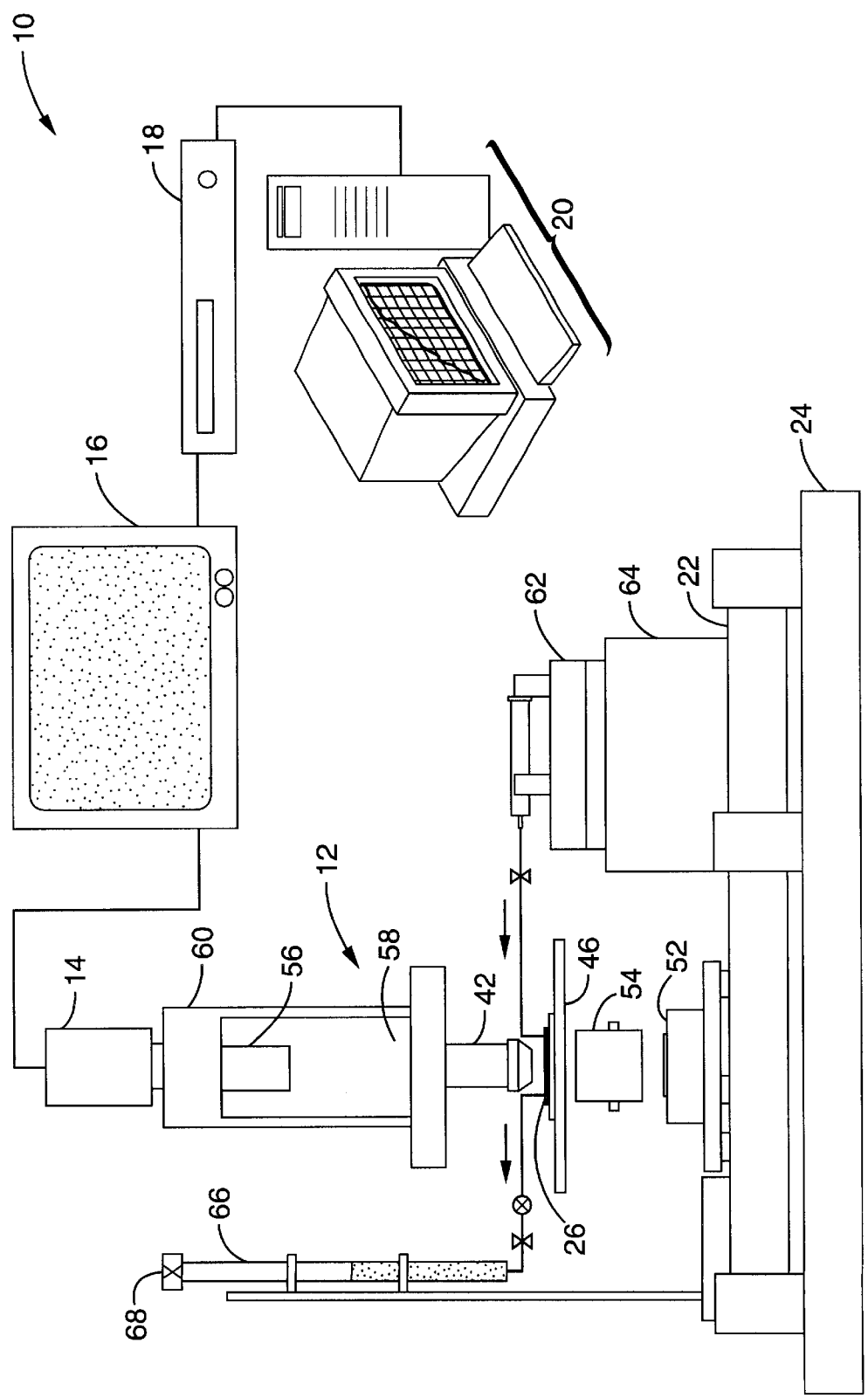
FIG. 1 is a schematic of an embodiment of an automated video microscopic imaging and data acquisition system according to the present invention.
Figure 4:
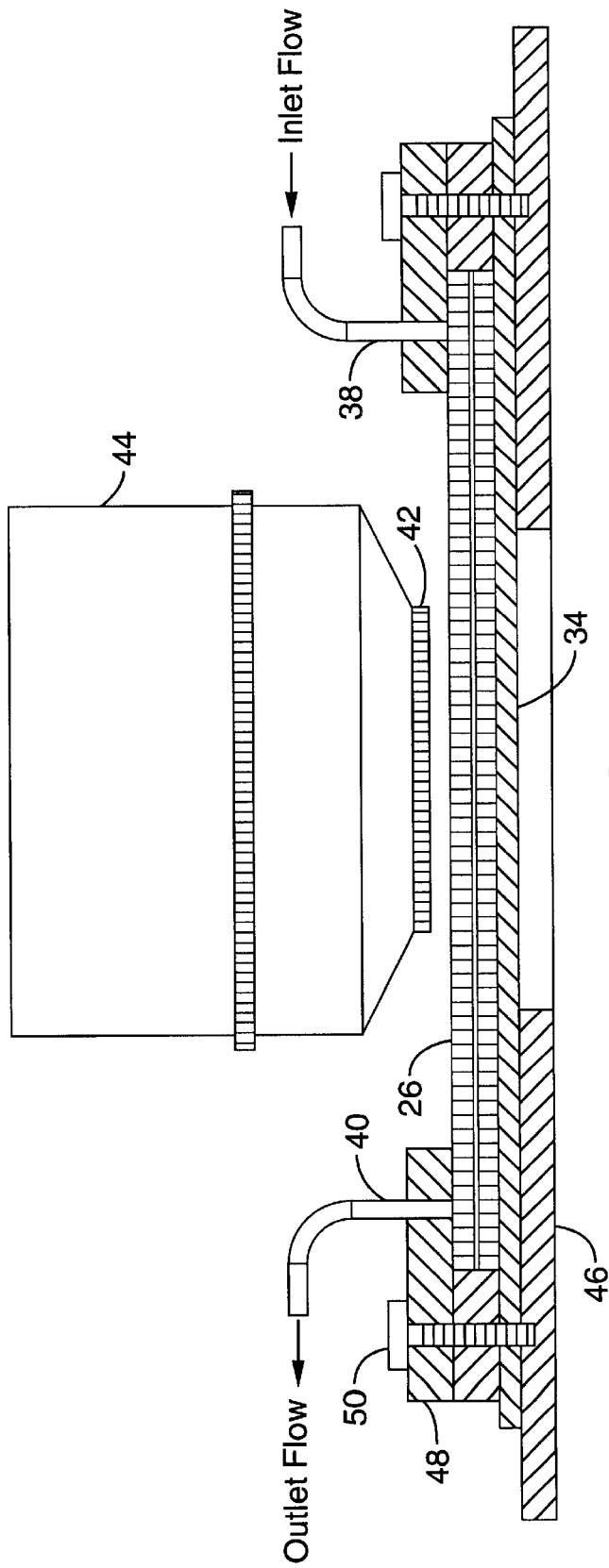
FIG. 4 is a partial enlarged view of the deposition cell and object lens portion of the system shown in FIG. 1.

Referring first to FIG. 1, a schematic diagram of an automated video microscopic imaging and data acquisition system 10 according to an embodiment of the invention is shown. The system shown in FIG. 1 comprises an optical microscope 12 equipped with a charge-coupled-device (CCD) camera 14, an optional video monitor 16, an optional video recorder 18, and a personal computer (PC) 20. To minimize the effect of vibrations, microscope 12 is set on a floating marble tabletop 22 placed on a heavy marble table 24 as shown. The system is setup to visualize colloids in a parallel-plate test cell 26. A suite of software routines executable on PC 20 automates image capturing, digitizing, enhancement, and processing to extract real-time quantitative data. These data include: (a) surface concentration and flux of deposited colloids, (b) surface concentration and flux of attached and detached colloids, (c) spatial and temporal distributions of colloids on the surface, and (d) concentration distribution of mobile colloids in the bulk suspension. The software routines manipulate the data to determine the surface concentration and flux of attached and detached colloids as functions of the length of the time interval between successive images, from which the surface concentration and flux of arriving and departing colloids is estimated.

3. Deposition Cell

Referring also to FIG. 2 and FIG. 3, system 10 uses parallel-plate flow cell 26 made of high-grade glass. Cell 26 is a single homogeneous unit, assembled by fusion without intermediate adhesives. Cell 10 is annealed after assembly to remove any residual strain from the fusing process. In the embodiment shown, cell 26 has a channel 28 that is approximately 4.0 cm long, 0.8 cm wide, and 0.02 cm high, with a standard tolerance of ±0.001 cm.

Because cell 26 has a narrow aperture 30 (~0.02 cm), colloids at its inner surfaces and those in the bulk suspension can be visualized, with minimal deterioration and equal contrast, without the need of an ultralong-working-distance objective lens. A field of view with comparable dimensions to the cell's aperture 30 can be easily obtained with a relatively low magnification (20× or 40×). The small dimensions of cell 10 and its relatively thick walls 32 (0.125 cm) ensure almost perfect parallel-plate geometry. The cell volume (0.058 cm$^3$) is very small, thus only a small amount of the colloidal suspension is required to perform an experiment for an extended period of time under flowing conditions. Also, since the cell is fused and non-demountable, its inner surfaces, at which colloid deposition is studied, are protected from scratching, contamination, or any static charging induced, for example, by wiper cleaning.

To view the same sector of the cell's surface in all experiments, a glass stage micrometer 34 with a 20 $\mu$m scale 36 is permanently attached to the bottom of cell 26 using flexible silicon adhesive. The gap between the stage micrometer and the cell is freed of air and any residual adhesive. Four of the stage micrometer's marks enclosing the sector of the surface to be viewed are selected. On the screen of monitor 16, these four marks are permanently marked as a reference. Before the start of an experiment, the view window is carefully adjusted so that the selected four marks of the stage micrometer coincide exactly with the four marks on the monitor's screen.

It will be appreciated that, in order to utilize test cell 26, a flow must be introduced through test cell 26. Accordingly, test cell 26 includes an inlet port 38 and an outlet port 40 coupled to channel 28. It will also be appreciated that it is necessary to clean the inner surfaces of test cell 26 and remove all deposited colloids after each experiment. To do so, a two-step method is preferably used. First, de-ionized water at room temperature with an entrapped air bubble is injected into the cell at a low flow rate (~1 ml/hr). The air bubble, which is comparable to the cell volume, fills the entire cell except for a thin liquid film that separates the bubble from the inner surfaces of the cell. The colloids deposited at these surfaces detach as they are captured irreversibly by the liquid-air interface. As the bubble traverses the cell sweeping its inner surfaces, all previously deposited colloids are detached and carried away by the bubble. The flow rate of the de-ionized water is then increased to ~8 ml/hr to sweep the detached colloids out of the cell. After that, the cell is placed in a 60° C. ultrasonic bath and de-ionized water at 60° C. is continuously injected through it for ~2 minutes at a relatively high flow rate of 1800 ml/hr. Finally, the cell is flushed with a diluted methanol solution, followed by a rigorous flushing with de-ionized water at room temperature. Viewing of the surfaces of the cleaned cell under the microscope confirm that they are completely devoid of colloids and/or dust contamination.

4. Video Microscopic Arrangement

Referring again to FIG. 1, the video microscopic arrangement in system 10 comprises an upright optical microscope 12, a high-resolution black-and-white CCD camera 14, a high resolution black-and-white video monitor 16, a super VHS video recorder 18, and a frame grabber card (e.g., image digitizer) installed in a high speed PC 20 with a large storage capacity. Dark-field illumination is employed to visualize the colloids at either the bottom or the top inner surface of the test cell and in the bulk suspension. Optical microscope 12, which is a conventional upright unit such as an Olympus BX40 or the like, preferably has either a 20× or 40× magnification objective lens (e.g., Olympus LCPlanF1), having numerical apertures (NA) of 0.40 or 0.60, respectively. Relatively sharp images of the in-focus colloids are obtained by partially correcting for the spherical aberrations induced by the thickness of upper glass plate of cell 26 (e.g., ~0.125 cm). This is accomplished by attaching a correction cap 42 (e.g., Cap-G2±0.5) to the objective lens 44. Deposition cell 26 is fastened to the microscope's stage 46 using stainless steel holders 48 and fasteners 50. Preferably, a 300-watt halogen bulb (not shown) is used to illuminate cell 26 from below. The light from the bulb passes through an adjustable iris diaphragm 52 and a dry dark-field condenser 54 (e.g., Olympus U-DCD), having a numerical aperture of 0.8 to 0.9. Dark-field illumination is created by allowing only the low-NA light scattered from the in-focus colloids to enter the microscope's objective lens. The iris diaphragm is adjusted to pass the minimum light intensity needed to uniformly illuminate the in-focus colloids, without affecting the image quality. This adjustment also helps minimize any thermal effects that may be caused by excessive illumination.

A 3.3× photo eyepiece 56 (e.g., Olympus PE 3.3×), installed in the microscope's straight phototube 58 (e.g., Olympus U-SPT), picks up the image delivered by the objective lens and projects it onto the chip of a monochrome RS-170CCD camera 14 (e.g., Cuhu 4912). CCD camera 14 is attached to phototube 58 through a 0.3× C-mount TV adapter 60 (e.g., Olympus U-PMTVC). The frame grabber card installed in PC 20 digitizes the analog output of the camera for simultaneous image processing and data extraction.

Figure 5:
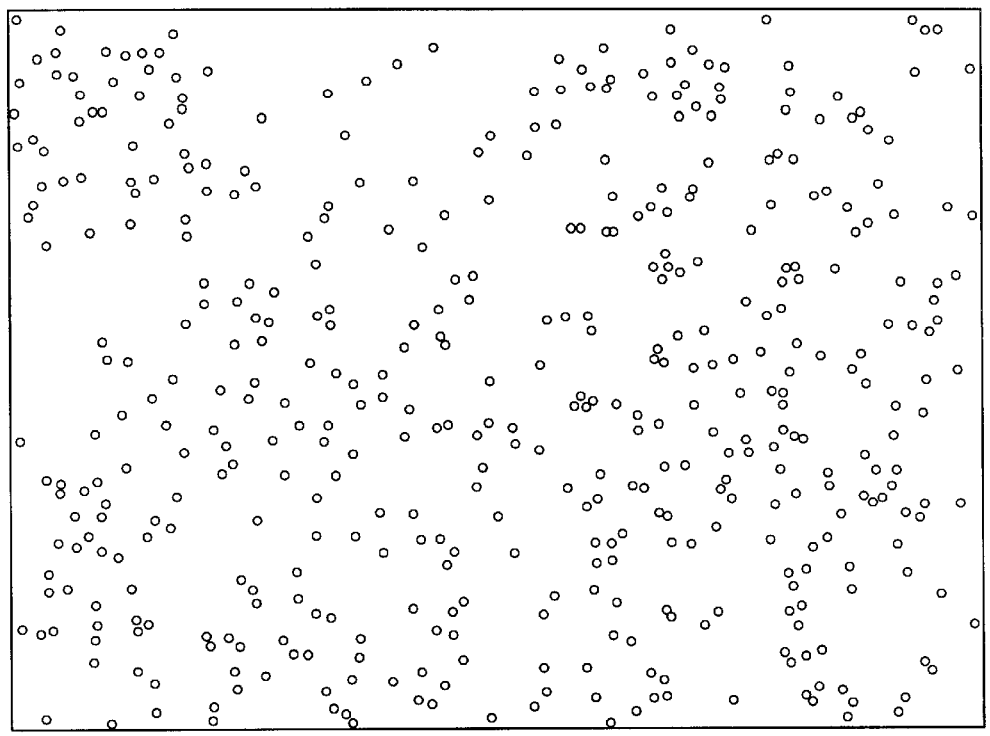
FIG. 5 is a diagram depicting a sample image of colloids at the top surface of a parallel-plate cell for 330-nm polystyrene fluorescent colloids using a 20× objective lens in a system according the present invention, where the negative of the image is shown.
Figure 6:
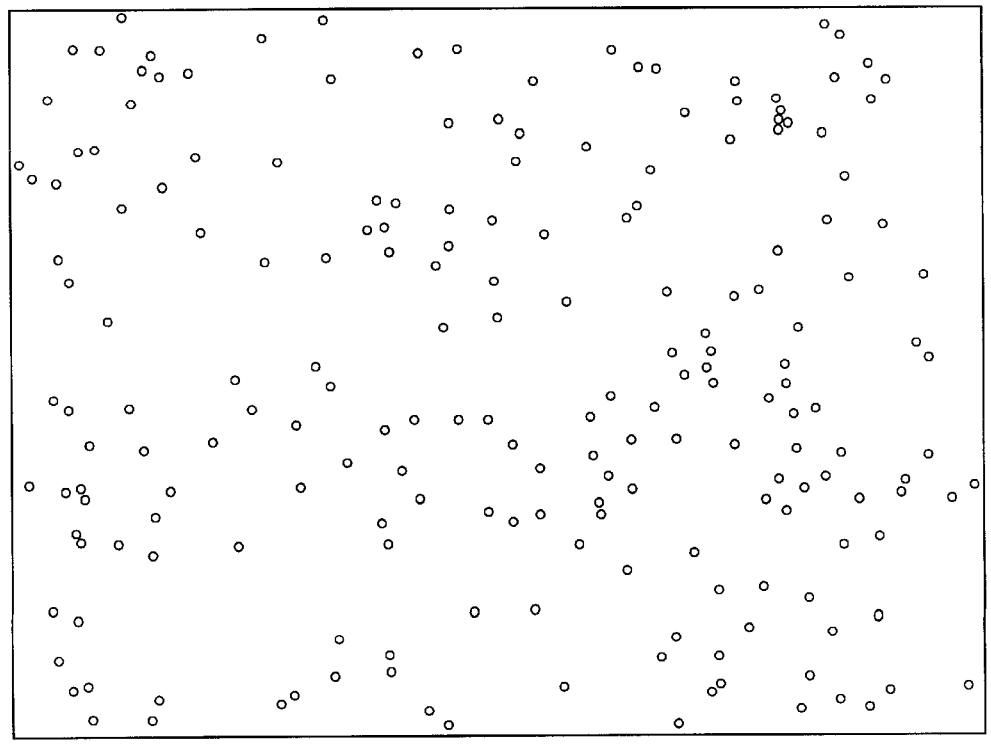
FIG. 6 is a diagram depicting a sample image of colloids at the top surface of a parallel-plate cell for 310 nm silica colloids using a 40× objective lens in a system according the present invention, where the negative of the image is shown.

By adjusting the angle of the incident light and correcting for optical aberrations, high contrast from the in-focus colloids is achieved, even though their size (~0.3 $\mu$m) is significantly smaller than the light wavelength ($\lambda \approx 0.546$ $\mu$m) and the microscope's resolution limit (~0.50 $\mu$m). Since the invention employs dark-field microscopy, the colloids in the captured images appear as bright "specks" against a dark background, with diffraction making them appear much larger than their actual size. This is diagrammatically depicted in FIG. 5 and FIG. 6, where reverse images are used for clarity in the drawings; that is, in FIG. 5 and FIG. 6 the colloids at the cell's top surface are shown as dark specks against a white background instead of white specks would be shown against a black background. FIG. 5 depicts test results for 330-nm polystyrene fluorescent colloids using the 20× object lens and FIG. 6 depicts test results for 310-nm silica colloids using the 40× objective lens. Although some colloids are immobile (deposited) and others are mobile (suspended), they all were found to have almost the same luminance values. The spatial resolution, $r_o$, of the system can be estimated from:

$$r_o = \frac{1.22\lambda}{NA_{obj} + NA_{cond}}. \tag{1}$$

Based on this equation, a spatial resolution of ~0.51 μm for the 20× objective and ~0.45 μm for the 40× objective is achieved, when the numerical aperture of the condenser, $NA_{cond}$, approaches 0.9. Test results verify that the visualized "specks" in the captured images of spherical colloids, 0.3 μm in diameter, are individual colloids.

The total linear magnification of the system is 19.8 and 39.6 for the 20× and the 40× objective lenses, respectively. The CCD camera's chip typically comprises 494 horizontal lines, with each line containing 768 active picture elements (pixels), and pixel being 8.4 μm by 9.8 μm. Thus, for the 20× and the 40× objective lenses, the areas of the image forming on the camera's chip are respectively:

$$S|_{20\times} = \left(\frac{768 \times 8.4 \times 10^{-4} \text{ cm}}{19.8}\right) \times \left(\frac{494 \times 9.8 \times 10^{-4} \text{ cm}}{19.8}\right) \approx 8 \times 10^{-4} \text{ cm}^2,$$

and $$S|_{40\times} = \left(\frac{768 \times 8.4 \times 10^{-4} \text{ cm}}{39.6}\right) \times \left(\frac{494 \times 9.8 \times 10^{-4} \text{ cm}}{39.6}\right) \approx 2 \times 10^{-4} \text{ cm}^2.$$

The actual size of the digitized image, calibrated against a 100-μm stage micrometer, measures $8.1378 \times 10^{-4}$ cm$^2$ and $2.03 \times 10^{-4}$ cm$^2$ for the 20× and the 40× objective lenses, respectively.

The above optical arrangements provide a relatively large depth of field of ~1.5 μm. This means that in-focus colloids could be distributed over a 1.5-μm thick layer of the suspension. As a result, deposited (immobile) colloids on the surface will have the same luminance value as those mobile within 1.5 μm from the surface. Therefore, in order to distinguish the immobile from the mobile colloids at the surface, an additional binary operation (described later) is used, particularly since traditional image segmentation above a certain luminance value is not sufficient.

5. Data Extraction Methodology

Figure 7:
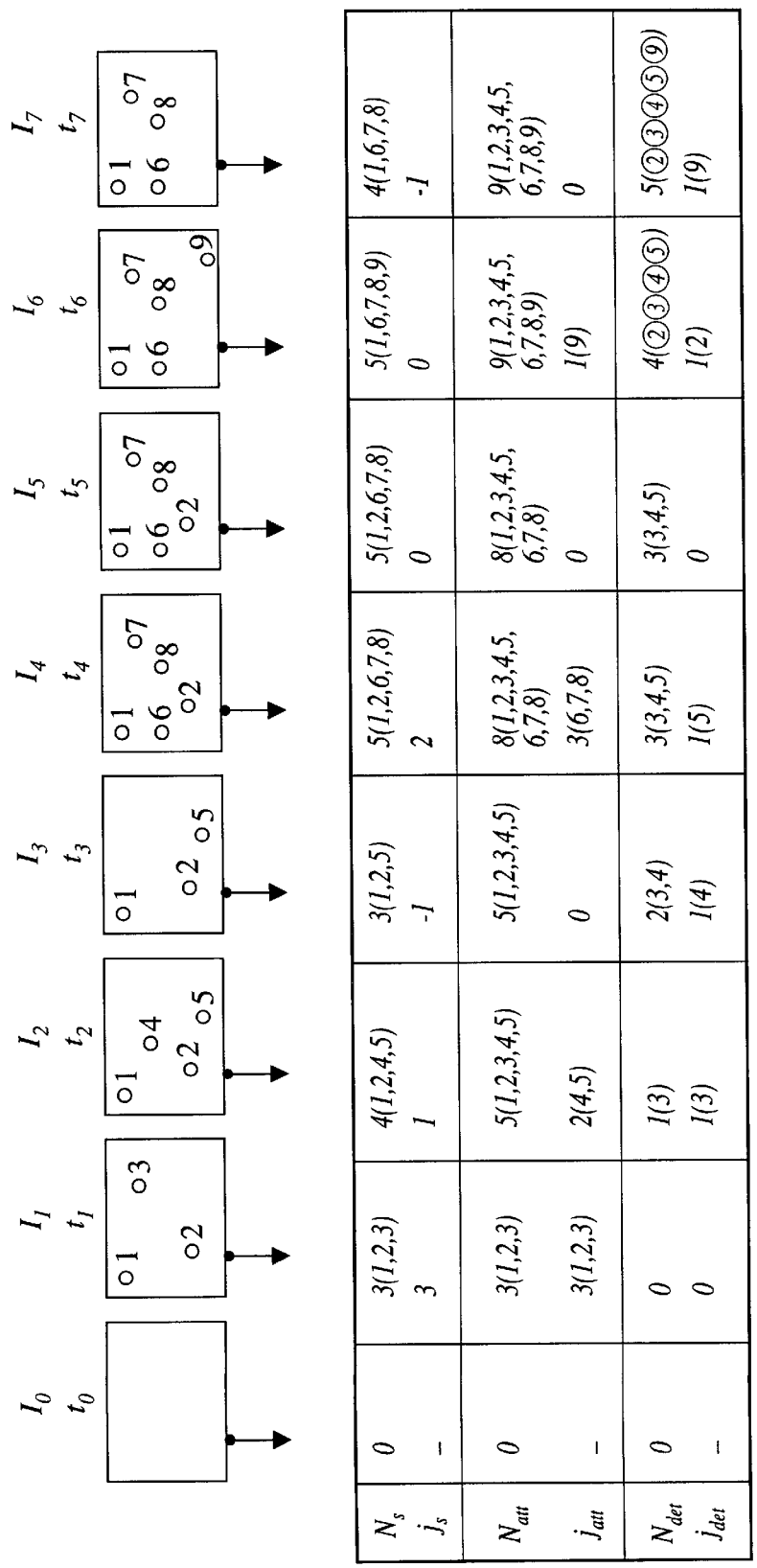
FIG. 7 is a diagram illustrating a method for determining the surface concentration and flux of deposited, attached, and detached colloids according to the present invention where italic numbers between brackets denote the "identity" of colloids.

FIG. 7 presents an illustrative example of the methodology used to determine the surface concentration and flux of deposited, attached, and detached colloids from the captured images at the surface. The example assumes a sequence of eight images, $I_0$ to $I_7$, of deposited colloids within an area S of the surface, captured at times $t_0, t_1, \ldots, t_7$, respectively. At $t_0$ the surface is completely devoid of colloids. The area S and the time interval between subsequent images, $\Delta\tau$, are constants and are equal to 1-cm$^2$ and 1-s, respectively.

The surface concentration, $N_s(t)$, of deposited colloids at any given time t, is:

$$N_s(t) = N_{att}(t) - N_{det}(t), \tag{2}$$

Differentiating Equation (2) with respect to time gives the colloid deposition flux as:

$$j_s(t) = j_{att}(t) - j_{det}(t). \tag{3}$$

The experimental estimate of the concentration of deposited colloids, $N_s(t_i)$, is directly obtained from counting the immobile colloids at $t_i$ in the area S. The corresponding colloid deposition flux, $j_s(t_i)$, is estimated from the counts from two successive images captured at $t_{i-1}$ and $t_i$, as:

$$j_s(t_i) = \frac{N_s(t_i) - N_s(t_{i-1})}{t_i - t_{i-1}}. \tag{4}$$

As this equation indicates, $j_s$ is negative when $N_s(t_i) < N_s(t_{i-1})$, positive when $N_s(t_i) > N_s(t_{i-1})$, and zero when $N_s(t_i) \approx N_s(t_{i-1})$.

The concentration of the attached colloids, $N_{att}(t_i)$, is obtained by counting all the attachment events that have ever taken place in the surface area S from $t_0$ and $t_i$. The corresponding colloid attachment flux, $j_{att}(t_i)$, is estimated as:

$$j_{att}(t_i) = \frac{N_{att}(t_i) - N_{att}(t_{i-1})}{t_i - t_{i-1}}, \tag{5}$$

The concentration of the detached colloids, $N_{det}(t_i)$, is obtained by counting all the detachment events that have ever taken place in the surface area S between $t_0$ and $t_i$. The corresponding colloid detachment flux, $j_{det}(t_i)$, is estimated as:

$$j_{det}(t_i) = \frac{N_{det}(t_i) - N_{det}(t_{i-1})}{t_i - t_{i-1}}. \tag{6}$$

Theoretically, the net surface concentration of the deposited colloids, $N_s(t)$, the sum of all the colloids attached to the surface between times $\tau$ and $\tau+\Delta\tau$ and remained attached up until time t, is given by the convolution:

$$N_s(t) = \int_0^t j_{att}(\tau) P(t-\tau) d\tau. \tag{7}$$

In this equation, $P(t-\tau)$ is the sticking probability at time t. It is the probability that a colloid attached to the surface between times $\tau$ and $\tau+\Delta\tau (\Delta\tau \ll t-\tau)$ remains attached until time t. The time interval $(t-\tau)$ is the residence time or the "age" of an attached colloid at time t. The discrete version of Equation (7) is:

$$N_s(t_m) = \sum_{i=1}^{m} j_{att}(t_i) \times P(t_i - t_{i-1}|t_m) \times (t_i - t_{i-1}). \tag{8}$$

Here, the quantity $P(t_i-t_{i-1}|t_m)$ is the probability that a colloid attached to the surface between times $t_{i-1}$ and $t_i$ remains attached up until $t_m$.

Applying Equation (8) to the illustrative example delineated by the set of images $I_0$ through $I_6$ in FIG. 7, gives the surface concentration of deposited colloids at time $t_6$ as:

$$N_s(t_6) = \sum_{i=1}^{6} j_{att}(t_i) \times P(t_i - t_{i-1}|t_6) \times (t_i - t_{i-1}),$$

where: $P(t_1 - t_0|t_6) = \frac{1(1)^*}{3(1, 2, 3)}$, $P(t_2 - t_1|t_6) = \frac{0}{2(4, 5)}$, $P(t_3 - t_2|t_6) = 0$, $P(t_4 - t_3|t_6) = \frac{3(6, 7, 8)}{3(6, 7, 8)}$, $P(t_5 - t_4|t_6) = 0$, and $P(t_6 - t_5|t_6) = \frac{1(9)}{1(9)}$.

The Italic numbers between brackets denote the "identity" of each particle. Hence:

$$N_s(t_6) = 3(1, 2, 3)\frac{1(1)}{3(1, 2, 3)} + 2(4, 5)\frac{0}{2(4, 5)} +$$
$$0 + 3(6, 7, 8)\frac{3(6, 7, 8)}{3(6, 7, 8)} + 0 + 1(9)\frac{1(9)}{1(9)}$$
$$= 1(1) + 3(6, 7, 8) + 1(9) = 5(1, 6, 7, 8, 9),$$

which can readily be verified from the example in FIG. 7.

From Equation (7), the colloid deposition flux, $j_s(t)$, can be expressed as:

$$j_s(t) = \int_0^t j_{att}(\tau)\frac{d}{dt}P(t-\tau)d\tau, \tag{9}$$

and in a discrete form as:

$$j_s(t_m) = \sum_{i=1}^{m} j_{att}(t_i)\left[\frac{P(t_i - t_{i-1}|t_m) - P(t_i - t_{i-1}|t_{m-1})}{t_m - t_{m-1}}\right](t_i - t_{i-1}). \tag{10}$$

Using this equation, the colloid deposition flux at time $t_6$ can be estimated from the set of images $I_0$ through $I_6$ in FIG. 7 as:

$$j_s(t_6) = \sum_{i=1}^{6} j_{att}(t_i)\left[\frac{P(t_i - t_{i-1}|t_6) - P(t_i - t_{i-1}|t_5)}{t_6 - t_5}\right](t_i - t_{i-1}),$$

where: $P(t_1 - t_0|t_5) = \frac{2}{3}$, $P(t_2 - t_1|t_5) = \frac{0}{2}$, $P(t_3 - t_2|t_5) = 0$, $P(t_4 - t_3|t_5) = \frac{3}{3}$, and $P(t_5 - t_4|t_5) = 0$.

Since $P(t_6-t_5|t_5)$ is undefined, i.e., equals to zero, hence:

$$j_s(t_6) = 3\left[\frac{1}{3} - \frac{2}{3}\right] + 2[0 - 0] + 0 + 3[1 - 1] + 0 + 1[1 - 0] = -1 + 1 = 0.$$

This value of the colloid deposition flux can also be verified from the example in FIG. 7.

Analogous to Equation (7), the theoretical estimate of $N_{det}(t)$, the sum of all colloids attached to the surface between times $\tau$ and $\tau+\Delta\tau$ and detached before some later time t, is given by the convolution:

$$N_{det}(t) = \int_0^t j_{att}(\tau)\hat{P}(t-\tau)d\tau. \tag{11}$$

In this equation, $\hat{P}(t-\tau)$ is the non-sticking probability at t, defined as the probability that a colloid attached to the surface between times $\tau$ and $\tau+\Delta\tau(\Delta\tau\ll t-\tau)$ detaches before some later time t. The relationship:

$$\hat{P}(t-\tau)=1-P(t-\tau), \tag{12}$$

is only valid if there were attachment between $\tau$ and $\tau+\Delta\tau$, otherwise, both $\hat{P}(t-\tau)$ and $P(t-\tau)$ are zero. The discrete version of Equation (11) is:

$$N_{det}(t_m) = \sum_{i=1}^{m} j_{att}(t_i) \times \hat{P}(t_i - t_{i-1}|t_m) \times (t_i - t_{i-1}), \tag{13}$$

Using this equation, the surface concentration of detached colloids at $t_6$ is:

$$N_{det}(t_6) = \sum_{i=1}^{6} j_{att}(t_i) \times \hat{P}(t_i - t_{i-1}|t_6) \times (t_i - t_{i-1}),$$

and from the set of images $I_0$ through $I_6$ in FIG. 7:

$\hat{P}(t_1 - t_0|t_6) = \frac{2(2, 3)}{3(1, 2, 3)}$, $\hat{P}(t_2 - t_1|t_6) = \frac{2(4, 5)}{2(4, 5)}$, $\hat{P}(t_3 - t_2|t_6) = 0$, $\hat{P}(t_4 - t_3|t_6) = \frac{0}{3(6, 7, 8)}$, $\hat{P}(t_5 - t_4|t_6) = 0$, and $\hat{P}(t_6 - t_5|t_6) = \frac{0}{1(9)}$.

Substituting these values into the above expression for $N_{det}(t_6)$ gives:

$$N_{det}(t_6) = 3(1, 2, 3)\frac{2(2, 3)}{3(1, 2, 3)} + 2(4, 5)\frac{2(4, 5)}{2(4, 5)} +$$
$$0 + 3(6, 7, 8)\frac{0}{3(6, 7, 8)} + 0 + 1(9)\frac{0}{1(9)}$$
$$= 2(2, 3) + 2(4, 5) = 4(2, 3, 4, 5).$$

From Equation (11), the colloid detachment flux, $j_{det}(t)$ can be written as:

$$j_{det}(t) = \int_0^t j_{att}(\tau)\frac{d}{dt}\hat{P}(t-\tau)d\tau, \tag{14}$$

and in a discrete form as:

$$j_{det}(t_m) = \sum_{i=1}^{m} j_{att}(t_i)\left[\frac{\hat{P}(t_i - t_{i-1}|t_m) - \hat{P}(t_i - t_{i-1}|t_{m-1})}{t_m - t_{m-1}}\right](t_i - t_{i-1}) \tag{15}$$

Using this equation, the experimental estimate of the colloid detachment flux at time $t_6$ is:

$$j_{det}(t_6) = \sum_{i=1}^{6} j_{att}(t_i)\left[\frac{\hat{P}(t_i - t_{i-1}|t_6) - \hat{P}(t_i - t_{i-1}|t_5)}{t_6 - t_5}\right](t_i - t_{i-1}),$$

and from the set of images $I_0$ through $I_6$ in FIG. 7:

$\hat{P}(t_1 - t_0|t_5) = \frac{1(3)}{3(1, 2, 3)}$, $\hat{P}(t_2 - t_1|t_5) = \frac{2(4, 5)}{2(4, 5)}$, $\hat{P}(t_3 - t_2|t_5) = 0$, $\hat{P}(t_4 - t_3|t_5) = \frac{0}{3(6, 7, 8)}$, $\hat{P}(t_5 - t_4|t_5) = 0$, and $\hat{P}(t_6 - t_5|t_5) = 0$.

Substituting these values into the above expression for $j_{det}(t_6)$ gives:

$$j_{det}(t_6) = 3(1, 2, 3)\left[\frac{2(2, 3) - 1(3)}{3(1, 2, 3)}\right] +$$

-continued $$2(4, 5)\left[\frac{2(4, 5) - 2(4, 5)}{2(4, 5)}\right] + 0 +$$

$$3(6, 7, 8)\left[\frac{0 - 0}{3(6, 7, 8)}\right] + 0 + 1(9)\frac{0}{1(9)}$$

$$= 1(2),$$

which can also be verified from the example in FIG. 7.

The above calculations verify the accuracy in defining the surface concentration and flux of deposited colloids using Equations (7) and (9), respectively, and those of the detached colloids using Equations (11) and (14), respectively.

6. Extraction of Experimental Data from Captured Images

Figure 8:
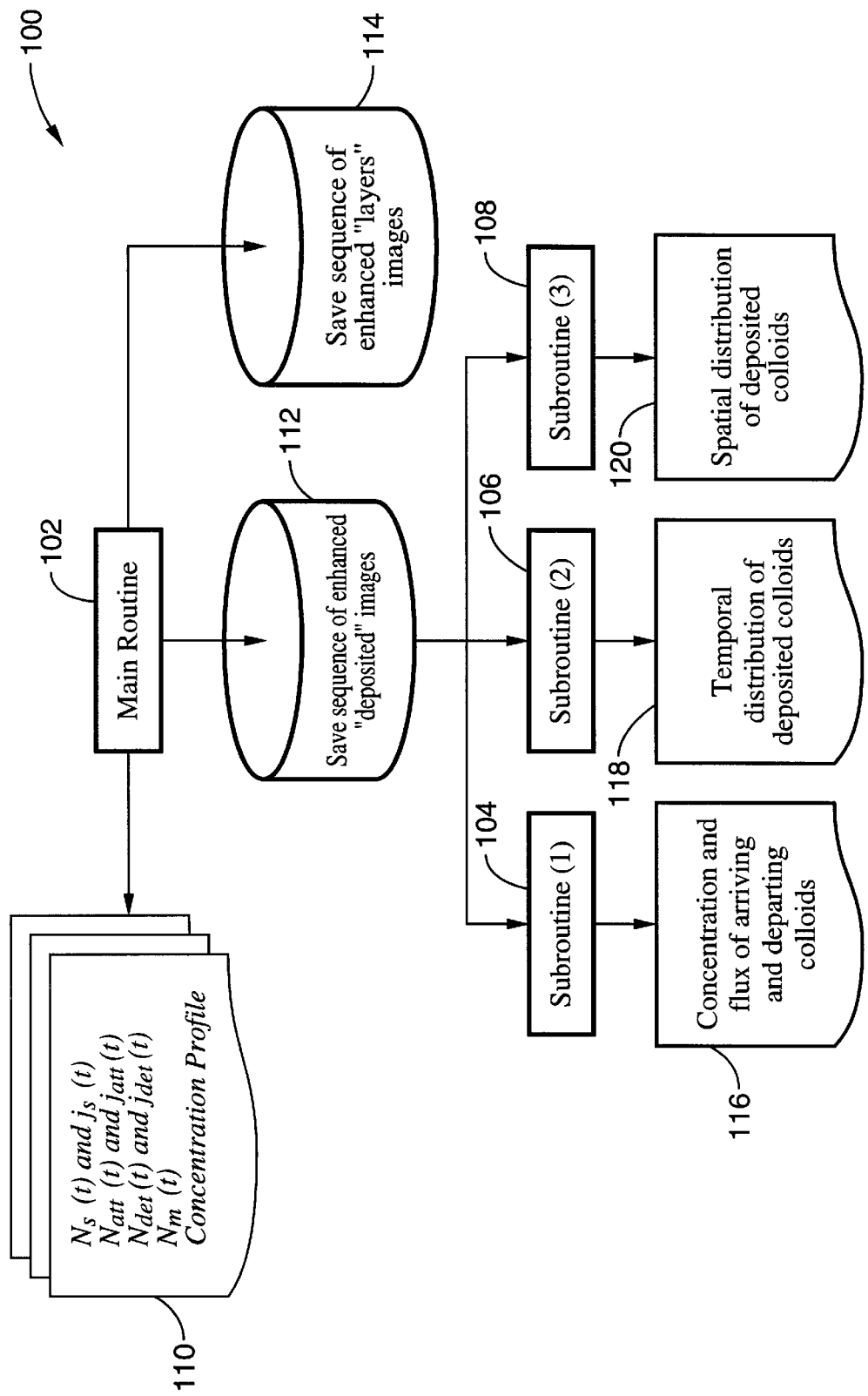
FIG. 8 is a diagram showing the. architecture of an embodiment of software employed in the system of the present invention.

Referring to FIG. 8, the invention also comprises a suite 100 of software routines that work as macros under the image analysis software Optimas 6.2 (Media Cybernetics, L.P.) to carry out an effective methodology for extracting different key quantities from images captured during a typical deposition experiment. Written in ALI (Analytical Language for Images), this suite of routines comprises a main routine 102 and three subroutines 104, 106, 108.

Main Routine 102 automatically acquires and analyzes thousands of images of in-focus colloids at the top or the bottom surface of the test cell or in the bulk suspension and produces a real-time graphical display of the extracted data 110. For example, Main Routine 102 acquires images of the interface at predefined time intervals, processes images for enhancement and features identification, discriminates between mobile and immobile particles, and extracts data in real time. Main Routine 102 then renders real-time graphical displays of extracted data that plot evolution of mobile and immobile colloids at the interface, cumulative concentration over time of colloids attaching to and detaching from the interface, and concentration profile of colloids across the suspension. Main Routine 102 also saves a sequence of images 112, referred to as "deposited" images, containing immobile colloids at the surface at different times during the experiment.

Optionally, main routine 102 saves a sequence of images 114, referred to as "layers" images, which contains colloids at different layers across the suspension, for direct quantification by classical tracking methods. This optional direct quantification routine determines (1) the average diffusion coefficient and velocity of colloids in different layers of the suspension and (2) the zeta potential of the colloids in different layers when a potential field is applied across the cell.

From the sequence of "deposited" images 112, the first subroutine, Subroutine 104, estimates the actual concentration and flux of attached and detached colloids, i.e., the surface concentration and flux of arrived and departed colloids 116. Subroutine 106 extracts the sticking probability function, $P(t-\tau)$, i.e., the temporal or adhesion time distribution of deposited colloids 118. Subroutine 108 determines the "normal" and "pair correlation" distribution functions of the deposited colloids, i.e., the spatial distribution of deposited colloids 120.

(a) Surface Concentration and Flux of Deposited, Attached, and Detached Colloids During the course of a typical colloid deposition experiment, Main Routine 102 enables real-time extraction of $N_s$, $N_{att}$, $N_{det}$, $j_s$, $j_{att}$, and $j_{det}$. Once this routine starts, it registers the start time and date of the experiment, and sends a signal to the CCD camera 14 to acquire an image, for example $I|_{t_i}$ at time $t_i$, shown in FIG. 9. The acquired image is automatically saved on the hard drive of PC 20 and a binary version is saved temporarily in the PC buffer. The centroids of the colloids (both mobile and immobile) in this image are identified as local luminance maxima and their number is counted and divided by the surface area S. After a specified time interval $\delta t_1$ is elapsed, a second image $I|_{t_i+\delta t_1}$ is acquired, binarized, and superimposed by a binary "AND" operation to the buffer binary image $I|_{t_i}$. Referring also to Table 1, the result of this "AND" operation is a new binary image, $I'|_{t_i}$, containing colloids which remained immobile at the surface between $t_i$ and $t_i+\delta t_1$. The surface concentration of deposited colloids at $t_i$ is then determined as:

$$N_s(t_i) = \frac{N\{I'|_{t_i}\}}{S} = \frac{N\{I|_{t_i} \text{ AND } I|_{t_i+\delta t_1}\}}{S}. \quad (16)$$

Image $I'|_{t_i}$ is saved on the PC hard drive as part of the "deposited" sequence of images and also kept temporarily in the PC buffer until the next iteration.

After another time interval $\delta t_2$ is elapsed, the above iteration is repeated to obtain image $I'|_{t_{i+1}}$. This image is then superimposed by a binary "OR" operation to the buffer image $I'|_{t_i}$ to obtain image $I''|_{t_{i+1}}$, which contains all colloids attached to the surface up until time $t_{i+1}$. The surface concentration of the attached colloids at time $t_{i+1}$ is then determined as:

$$N_{att}(t_{i+1}) = \frac{N\{I''|_{t_{i+1}}\}}{S} = \frac{N\{I'|_{t_{i+1}} \text{ OR } I'|_{t_i}\}}{S}. \quad (17)$$

Image $I''|_{t_{i+1}}$ is then subtracted from $I'|_{t_{i+1}}$ to obtain image $I'''|_{t_{i+1}}$, which contains all colloids detached from the surface up until time $t_{i+1}$. The surface concentration of detached colloids at time $t_{i+1}$ is then determined as:

$$N_{det}(t_{i+1}) = \frac{N\{I'''|_{t_{i+1}}\}}{S} = \frac{N\{I''|_{t_{i+1}} - I'|_{t_{i+1}}\}}{S}. \quad (18)$$

Through a dynamic data exchange (DDL) channel, the extracted values of $N_s$, $N_{att}$, and $N_{det}$ are sent to a spreadsheet (Excel 2000) and displayed graphically on real-time basis during the entire course of the experiment. The values of $j_s$, $j_{att}$, and $j_{det}$ are obtained from the recorded values of $N_s$, $N_{att}$, and $N_{det}$ using Equations (4), (5), and (6), respectively, and also displayed graphically on real-time basis.

The above iterations are automatically repeated every $\delta t_2$. The saved sequence of "deposited" images, taken every $\Delta\tau = \delta t_1 + \delta t_2$ of immobile colloids at the surface, is used by the three subroutines as described in the next subsections.

(b) Distribution of Suspended Colloids

At preset times during the experiment, the concentration profile of suspended colloids across the test cell is measured. The microscope is sequentially refocused on the different horizontal layers containing suspended colloids across the entire cell's aperture. At each layer, five images, 0.1-second apart, are acquired, binarized, and saved. The colloids in each of the five images are identified, counted, and the result is sent to a separate spreadsheet. The number of colloids in each layer is calculated as the arithmetic mean of the five counts. The mean number of colloids in each layer is plotted against the distance from one of the cell's surfaces to estimate the distribution profile of the suspended colloids at a given time during the experiment.

(c) Arrival and Departure Events

Even at the highest speed of thirty-three images per second, the attachment and detachment events that take place at the surface during the relatively short "blind" interval between images are missed. Depending on the length of this interval, more of these events are missed. Thus, the obtained values of $N_{att}(t_i)$, $N_{det}(t_i)$, $j_{att}(t_i)$, and $j_{det}(t_i)$ could be less than the actual values at time $t_i$. Therefore, experiments performed under the same exact conditions, but in which images are captured at different speeds would produce different values for $N_{att}$, $N_{det}$, $j_{att}$, and $j_{det}$.

The actual surface concentration of attached colloids up until $t_i$, $N^*_{att}(t_i)$, can be estimated as:

$$N^*_{att}(t_i) = \lim_{\Delta\tau \to 0} N_{att}(\Delta\tau)\big|_{t_i}, \quad (19)$$

and that of the surface concentration of detached colloids up until $t_i$, $N^*_{det}(t_i)$, can be estimated as:

$$N^*_{det}(t_i) = \lim_{\Delta\tau \to 0} N_{det}(\Delta\tau)\big|_{t_i}. \quad (20)$$

The corresponding actual attachment and detachment fluxes of colloids at $t_i$, $j^*_{att}(t_i)$ and $j^*_{det}(t_i)$, are given respectively as:

$$j^*_{att}(t_i) = \frac{dN^*_{att}(t_i)}{dt}, \text{ and} \quad (21)$$

$$j^*_{det}(t_i) = \frac{dN^*_{det}(t_i)}{dt}. \quad (22)$$

The actual surface concentration of colloids residing at the surface at $t_i$, $N^*_s(t_i)$, is then given by:

$$N^*_s(t_i) = N^*_{att}(t_i) - N^*_{det}(t_i), \quad (23)$$

and the corresponding flux is given by:

$$j^*_s(t_i) = j^*_{att}(t_i) - j^*_{det}(t_i). \quad (24)$$

Note that the values of $N^*_{att}$ (or $j^*_{att}$), $N^*_{det}$ (or $j^*_{det}$), and $N^*_s$ (or $j^*_s$) include those colloids having very small residence times (almost zero) at the surface, i.e., the colloids that arrived to, or collided with, the surface and immediately departed from it.

Therefore, $N^*_{att}$ and $j^*_{att}$ are regarded to as the surface concentration and flux of arriving colloids, $N^*_{det}$ and $j^*_{det}$ as those of departing colloids, and $N^*_s$ and $j^*_s$ as those of residing colloids, respectively. These values also represent the theoretical upper limits of the surface concentration and flux of attached, detached, and deposited colloids.

Figure 10:
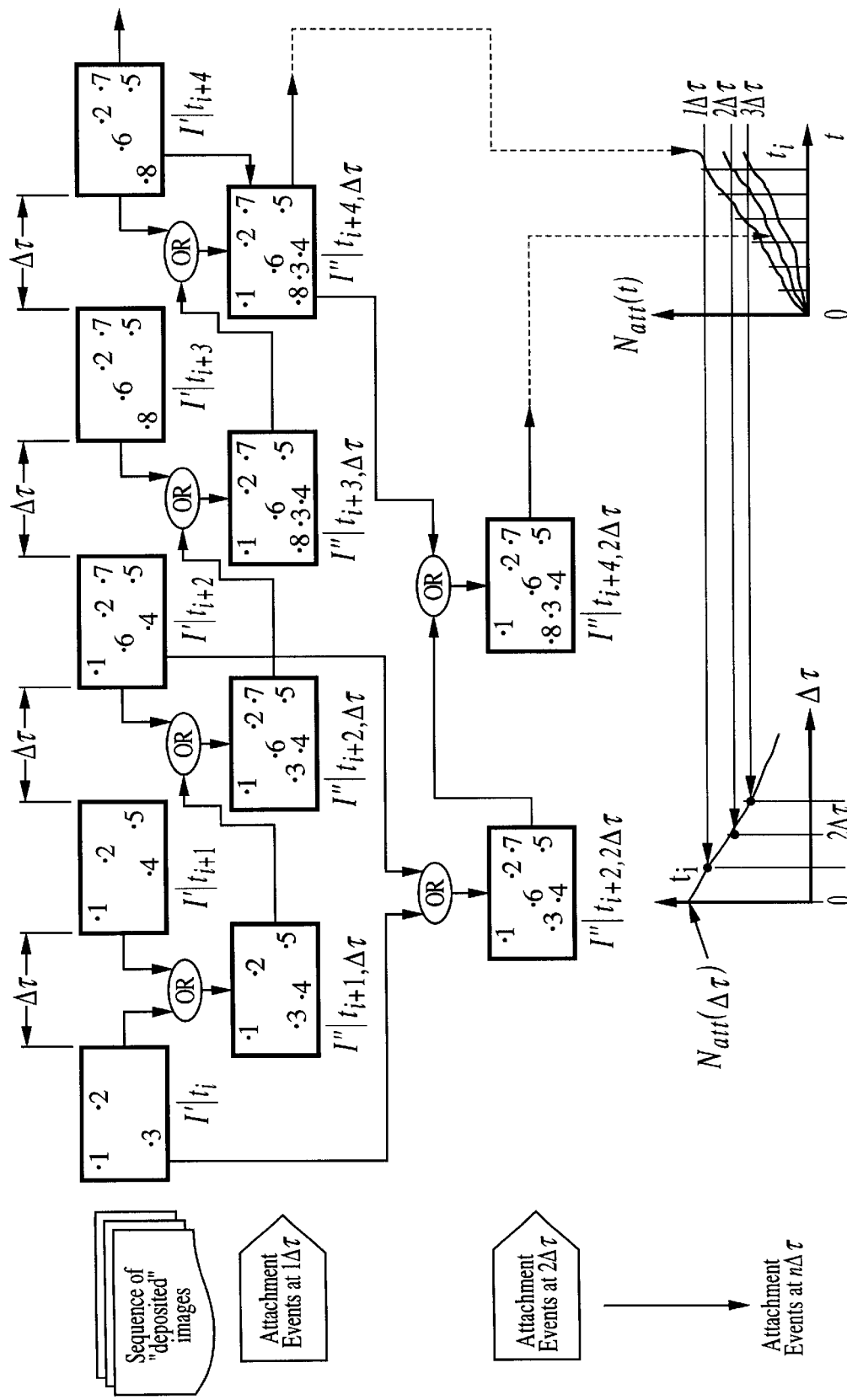
FIG. 10 is a flow and logic diagram showing a method for determining the concentration and flux of arriving and departing colloids in a parallel-plate test cell according to the present invention.

FIG. 10 illustrates the algorithm used by Subroutine 104 to estimate the arrival and departure events at the surface. Subroutine 104 uses the saved sequence of "deposited" images 112 to create several curves of the attachment and detachment events versus time, similar to the ones obtained by the main routine, but at different $\Delta\tau$ values. Data corresponding to selected times $t_i$ in the experiment are extracted from each curve to construct the relationships between $N_{att}(t_i)$, and $\Delta\tau$ and between $N_{det}(t_i)$, and $\Delta\tau$. A suitable model function is then fitted to the resulting ($N_{att}$–($\Delta\tau$)) and ($N_{det}$–($\Delta\tau$)) data points. For each value of $t_i$, this function is extrapolated to $\Delta\tau=0$ to obtain $N^*_{att}(t_i)$ and $N^*_{det}(t_i)$, respectively. Then, the corresponding values of $j^*_{att}(t_i)$ and $j^*_{det}(t_i)$ are determined using Equations (21) and (22), respectively. The values of $N^*_s(t_i)$ and $j^*_s(t_i)$ are readily determined from Equations (23) and (24), respectively.

(d) Temporal Distribution of Deposited Colloids

Using the sequence of "deposited" images, the temporal distribution of the colloids deposited onto the surface, i.e., the sticking probability distribution function, $P(t-\tau)$, is determined using Subroutine 106 as:

$$P(t_m - t_i) = \frac{N\{[I'|_{t_i} - I'|_{t_{i-1}}] \text{ AND } I'|_{t_m}\}}{N\{[I'|_{t_i} - I'|_{t_{i-1}}]\}}, \quad (25)$$

where $N\{I'|_{t_i}, I'|_{t_{i-1}}\} \neq 0$, for $i=1, 2, \ldots, m$. The binary operation $[I'|_{t_i} - I'|_{t_{i-1}}] \text{ AND } I'|_{t_m}$ results in a binary image containing those colloids attached to the surface between times $t_{i-1}$ and $t_i$, which remained attached up until $t_m$.

Subroutine 106 can also determine the "non-sticking" probability function at $t_m$ as:

$$\hat{P}(t_m - t_i) = 1 - \frac{N\{[I'|_{t_i} - I'|_{t_{i-1}}] \text{ AND } I'|_{t_m}\}}{N\{[I'|_{t_i} - I'|_{t_{i-1}}]\}}, \quad (26)$$

where $N\{I'|_{t_i} - I'|_{t_{i-1}}\} \neq 0$, for $i=1, 2, \ldots, m$.

(e) Spatial Distribution of Deposited Colloids

The spatial distribution of deposited colloids provides important information on the heterogeneity of the surface and the range and nature of the interaction between deposited colloids. Subroutine 108 uses the sequence of "deposited" images 112 to determine the spatial distribution of deposited colloids at the surface at predefined times during the experiment in different forms.

Figure 11:
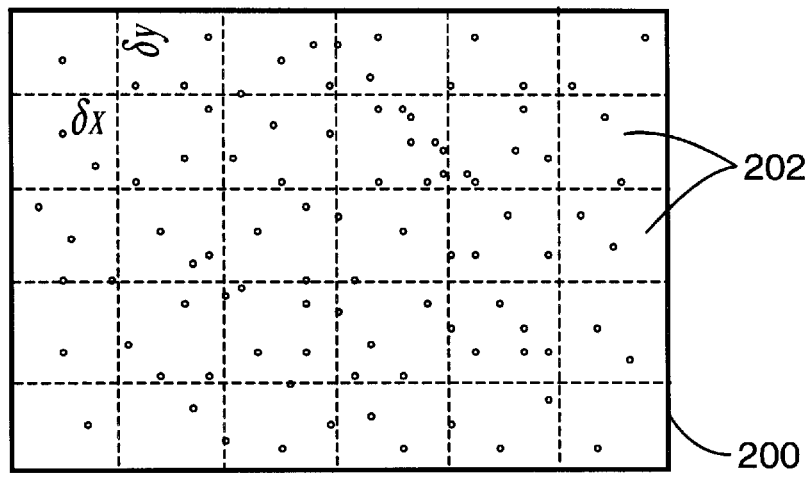
FIG. 11 is a schematic illustration depicting a method for determining the normal distribution of deposited colloids according to the present invention.

The subroutine determines the distribution function, $P_N$, of deposited colloids as the probability density of finding a region, within the observed area S, containing a certain number of colloids, N. Referring to FIG. 11, the observed surface area S in the original image 200 is first divided into small equal regions 202 and the number of colloids, N, in each region is counted. Consequently, $P_N$ is calculated as the number of regions containing N colloids divided by the total number of regions within the observed area S.

Figure 12:
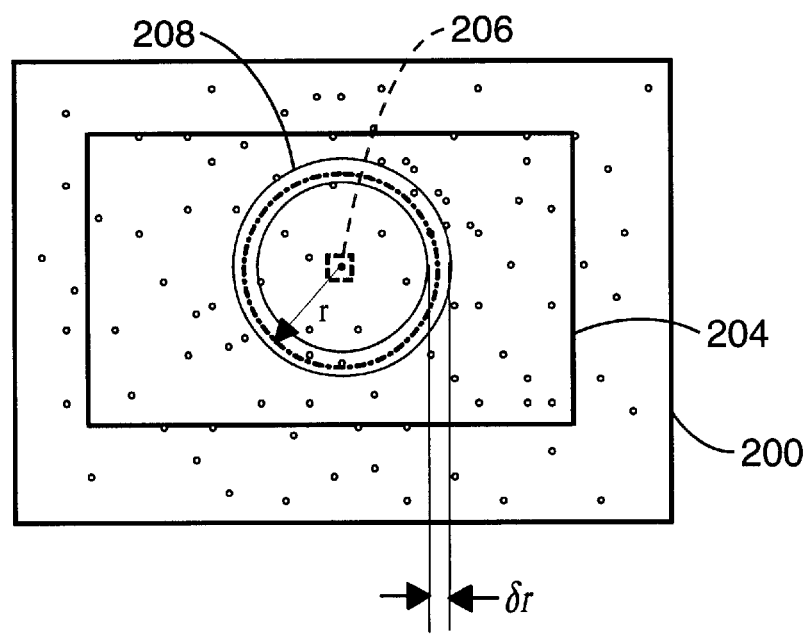
FIG. 12 is a schematic illustration depicting a method for determining the radial pair distribution of deposited colloids according to the present invention.

Referring also to FIG. 12, Subroutine 108 also determines the radial pair distribution function, g(r), of deposited colloids at the surface. A rectangular core region 204 within the observed surface area S is first selected and the coordinates of all stationary colloids in that region are defined. Each $i^{th}$ colloid 206 in this core region is employed once as the center of a circular shell 208 of radius r and thickness $\delta r$ and the number of colloids in the shell is counted. Consequently, g(r) is determined as:

$$g(r) = \frac{\sum_{i=1}^{N} N_i(r, \delta r)}{N \, A_{Shell}(r, \delta r)} \times \frac{A_{Tot}}{N}. \quad (29)$$

In this formula, N is the total number of colloids in the core region 204, $A_{Tot}$ is the area of that region, $N_i$ is the number of colloids in the shell 208, and $A_{shell}$ is the area of the shell 208.

7. Connectivity

Figure 13A:
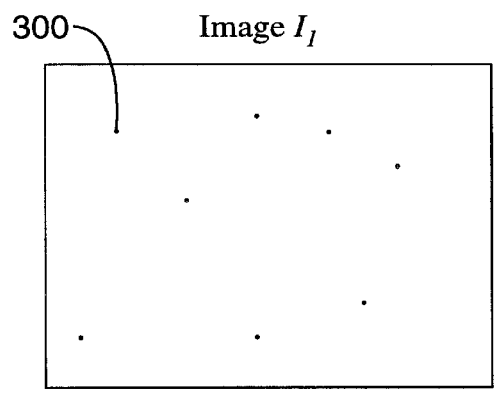
FIG. 13A through FIG. 13E depict binary operations on unconnected shifted images of colloids according to the present invention, where the negatives of the images are shown.
Figure 13B:
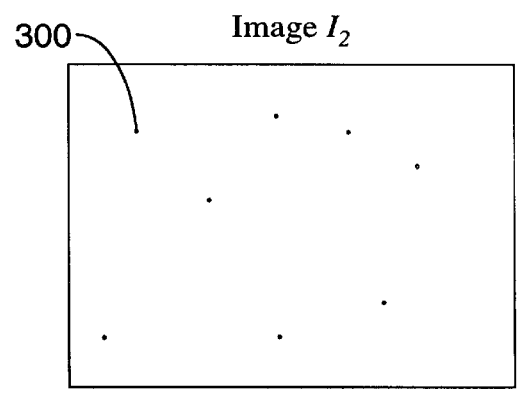
Figure 13C:
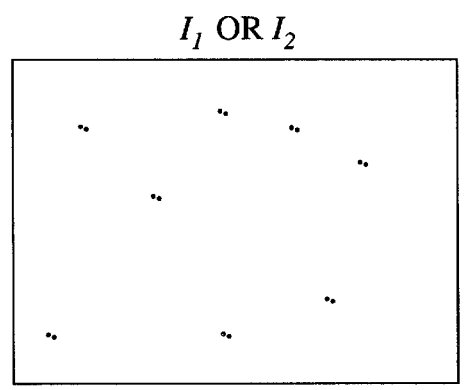
Figure 13D:
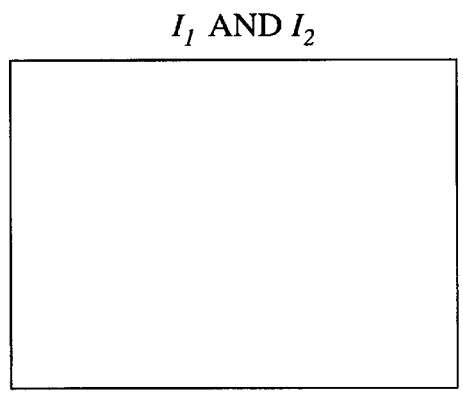
Figure 13E:
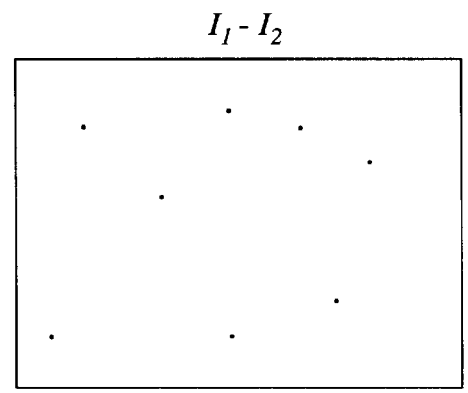

Connectivity means that an immobile colloid in one image corresponds to the same colloid in subsequent images, provided that the colloid remains attached at the same location on the surface. Since extracting different deposition quantities is based on comparing images taken over long periods of time, it is important to establish connectivity between these images. Losing connectivity between subsequent images results when the field of view shifts over time, perhaps due to vibrations or inadvertent movement of the imaging optics. The errors that result when connectivity is not established between subsequent images in an experiment are manifested by the example in FIG. 13. In this example, image $I_1$ (FIG. 13A) contains eight deposited colloids, while image $I_2$(FIG. 13B) contains the same eight colloids in image $I_1$, but the observed field is intentionally shifted by a random amount. The resulting images after "OR", "AND", and "Subtract" binary operations, required by the subroutines, are shown in FIG. 13C, FIG. 13D and FIG. 13E, respectively. Again, for purposes of clarity in the drawing figures the colloids are shown as dark specs against a white background while although the invention will display the colloids as white specs against a black background. The counts from these images, shown in Table 2, clearly demonstrate that poor connectivity produces erroneous results.

Referring also to FIG. 14, to establish connectivity in the present routines, a "moving window" method is applied before superimposing the subsequent images. Referring first to FIG. 14A, in this method an immobile colloid 300 within the observed region of interest (roi) 302 is selected as a reference, and the x-y coordinates of its centroid are determined. A new roi 304, having fixed length and height slightly smaller than those of the original roi 302 is created by defining the x-y coordinates of two of its opposite corners relative to the x-y coordinates of the centroid of the reference colloid 300. The x-y coordinates of the upper-left corner of this new roi 304 are employed as the origin to which the x-y coordinates of all colloids within the new roi 304 are related. Referring to FIG. 14B, in the subsequent image the same reference colloid 300 is located, a roi having the same length and height as the roi in the previous image is created in the same manner. Similarly, the x-y coordinates of the colloids within the roi are related to its upper-left corner. The desired binary operations are performed on the new identical regions of interest, rather than the full images.

Figure 14A:
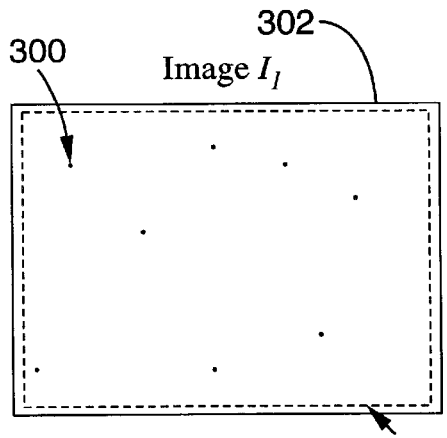
FIG. 14A through FIG. 14E correspond to the images of FIG. 13A through FIG. 13E after establishing connectivity.
Figure 14B:
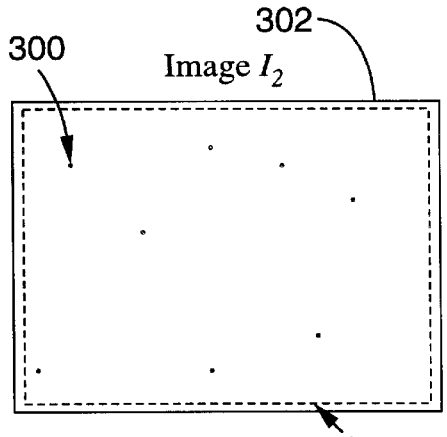
Figure 14C:
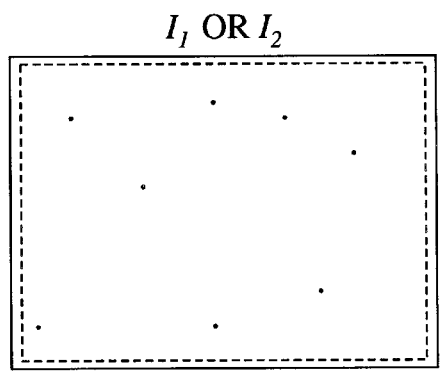
Figure 14D:
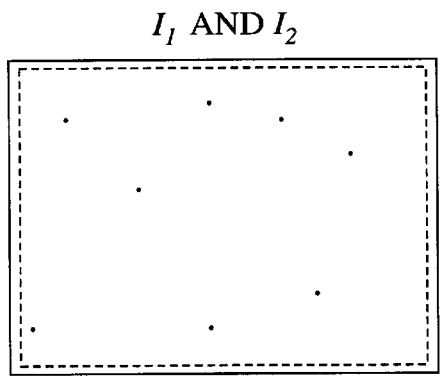
Figure 14E:
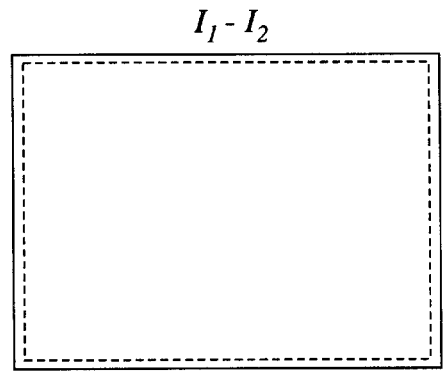

FIG. 14C, FIG. 14D and FIG. 14E, respectively, show the resulting images after "OR", "AND ", and "Subtract" binary operations on the same images in FIG. 13, but when connectivity is established using the above "moving window" method. The counts obtained from these images are shown in Table 2. Obviously, when connectivity is established using the "moving window" method, the correct counts of the colloids in the images are resembled.

To avoid losing connectivity in case the reference colloid moves, a group of immobile colloids is chosen to establish a frame of reference for all images. If, in later images, the reference colloid moves, another colloid in the group of immobile colloids is selected as the new reference and the new roi is mapped to the previous roi.

EXAMPLE 1

Representative Results

In this section, typical experimental results, obtained using the system and data extraction routines of the present invention, are presented. These results are for an experiment on the deposition of polystyrene latex spherical colloids (330-nm in diameter) onto the top surface of the test cell. The colloids are dispersed fresh before the experiment in a synthetic groundwater having a pH of ~8 and ionic strength of 0.05 M at a bulk concentration of $2 \times 10^8$ cm$^{-3}$. Referring again to FIG. 1, the colloidal suspension is pumped continuously for ~4 days through the test cell 26, using a pulse-free syringe pump 62, at a flow rate of 0.04 ml/hr (an average flow velocity of $6.94 \times 10^{-4}$ cm/s). For support, syringe pump 62 is attached to a foam block 64 which is in turn attached to floating table 22. To ensure pulse-free flow in the cell, a volumetric pipette 66 having a one-way valve 68 was attached to the cell's outlet. Prior to the experiment, the surfaces of the cell were preconditioned by pumping a particle-free synthetic groundwater for twenty-four hours through the cell at a flow rate of 1 ml/hr.

Figure 15:
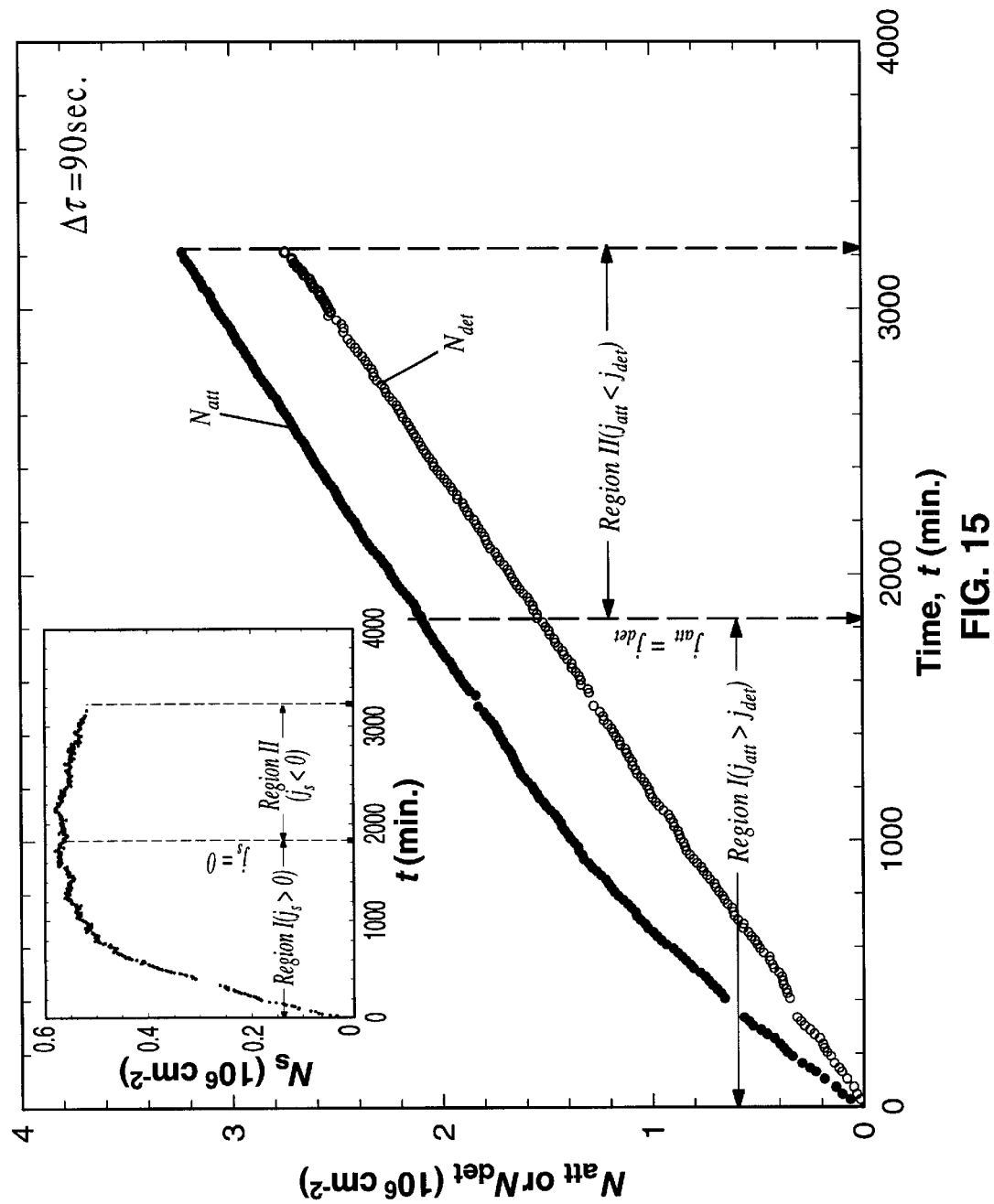
FIG. 15 is a graph of experimental results showing the relationship between values of $N_s$, $N_{att}$, and $N_{det}$, obtained on real-time basis during the deposition experiment at different times wherein the inset shows the change of $N_s$, the filled circles represent $N_{att}$, and the open circles represent $N_{det}$.
Figure 16:
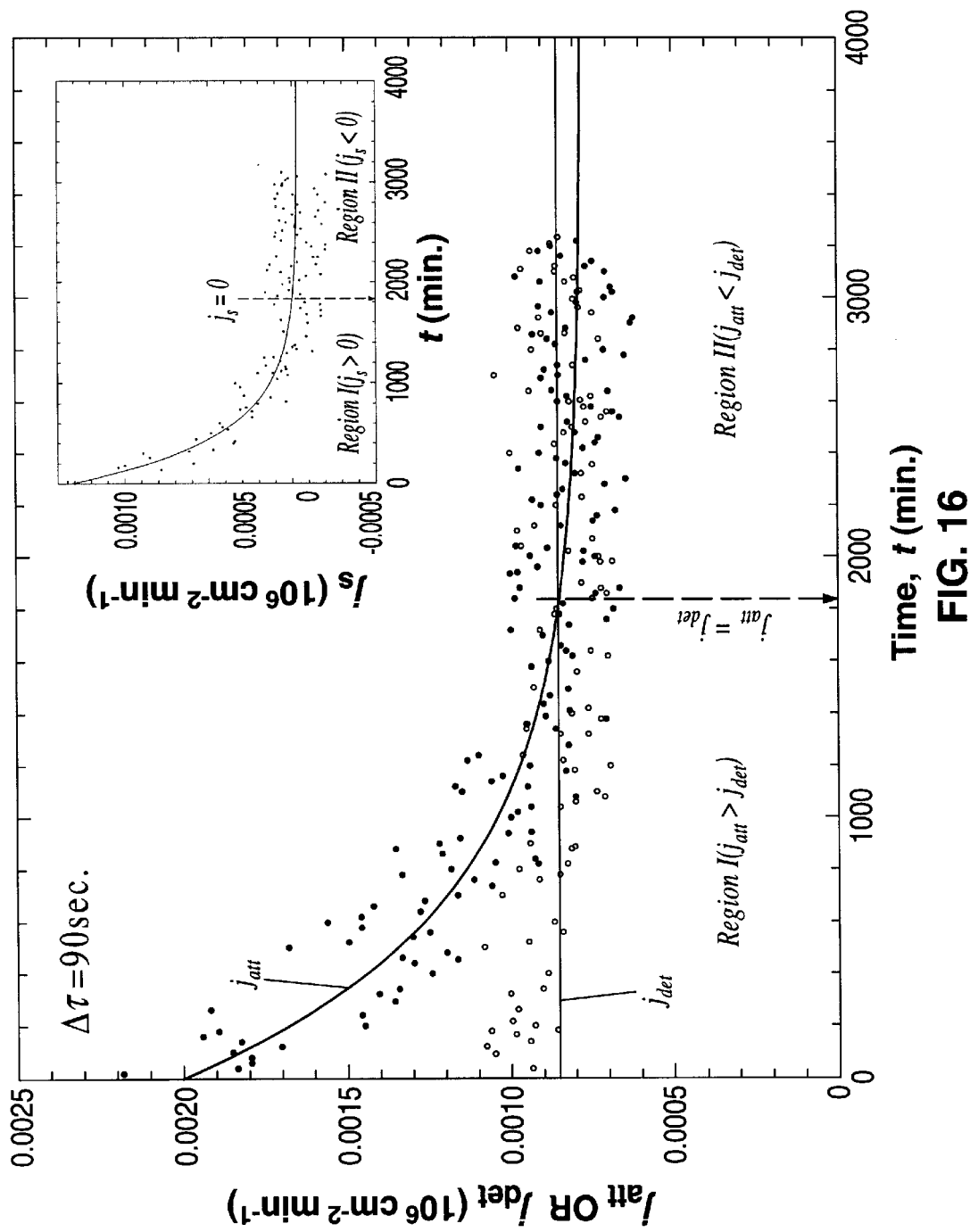
FIG. 16 is a graph of experimental results showing the relationship between the values of $j_s$, $j_{att}$, and $j_{det}$, obtained on real-time basis during the deposition experiment at different times, wherein the inset shows $j_s$, the filled circles represent $j_{att}$, the open circles represent $j_{det}$, and the solid lines are provided for visual guidance.

(a) Surface Concentration and Flux of Deposited, Attached, and Detached Colloids FIG. 15 and FIG. 16 represent the values of $N_s$, $N_{att}$, $N_{det}$, $j_s$, $j_{att}$, and $j_{det}$, obtained on real-time basis during the deposition experiment at different times. In FIG. 15, the inset shows the change of $N_s$, the filled circles represent $N_{att}$, and the open circles represent $N_{det}$. In FIG. 16, the inset shows $j_s$, the filled circles represent $j_{att}$, and the open circles represent $j_{det}$. The solid lines in FIG. 16 are provided for visual guidance.

The data points in these two figures are obtained when the time between captured images, $\Delta \tau$, is ninety seconds. Unlike the experimental data points of the surface concentrations (FIG. 15), those of the surface fluxes (FIG. 16) show considerable scattering. This scattering is most likely because the frequency of image capturing does not coincide with that of the attachment and detachment events of the colloids at the surface. Less scattering data are possible at lower image capturing frequencies, so that the number of attachment and detachment events are averaged over longer time intervals. A drawback of increasing the image capturing frequency, however, is missing a larger number of the attachment and detachment events taking place during the blind period between images.

An examination of FIG. 15 and FIG. 16 reveals that, for the first ~1400 minutes, $N_{att}$ increases ($j_{att}$ decreases) non-linearly with time at a declining rate. Beyond ~1400 minutes, $N_{att}$ increases with time almost linearly ($j_{att}$ reaches an asymptotic value >0). On the other hand, $N_{det}$ increases almost linearly (constant $j_{det}$>0) with time for the entire duration of the experiment. These figures also show that $N_s$(the difference between $N_{att}$ and $N_{det}$) increases, while $j_s$ (the difference between $j_{att}$ and $j_{det}$) decreases with time at a declining rate for the first ~1800 minutes. At ~1800 minutes, $N_s$ reaches a maximum (i.e., $j_s$~0), as $j_{att}$ and $j_{det}$ become equal. Beyond ~1800 minutes, however, $j_{att}$ drops below $j_{det}$, thus $N_s$decreases (i.e., $j_s$<0).

Based on the data in FIG. 15 and FIG. 16, it can be seen that the colloid deposition process exhibits different regions. In this particular example, two distinct regions can be identified: Region I ($j_{att}$>$j_{det}$), in which colloid deposition is dominated by the attachment to the surface and Region II ($j_{att}$<$j_{det}$), where the deposition is dominated by the detachment from the surface.

(b) Bulk Concentration of Mobile Particles

Figure 17:
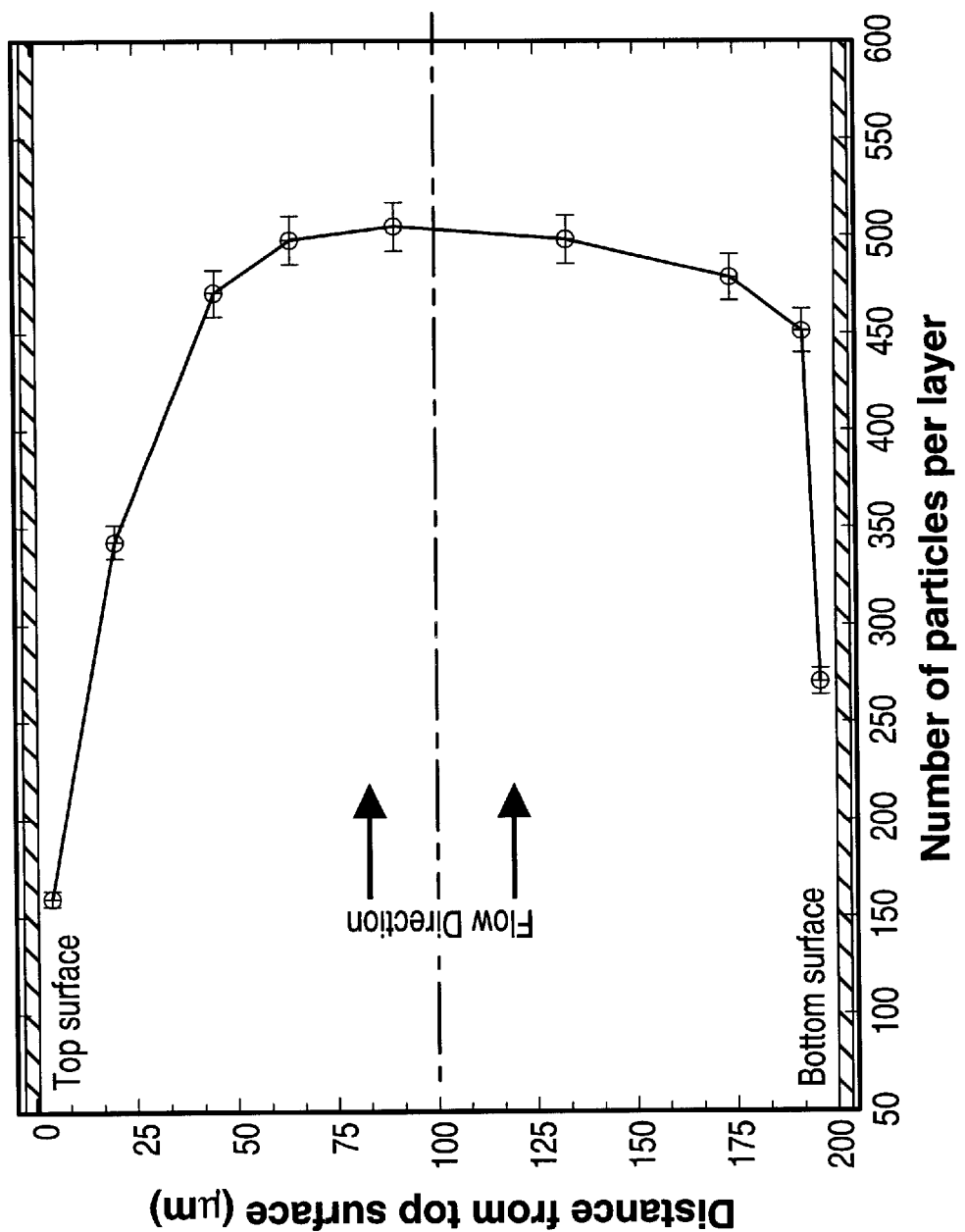
FIG. 17 is a graph of experimental results showing the distribution of colloid concentration across the bulk suspension at t~300 minutes.

FIG. 17 shows the measured profile of the average number of mobile colloids at different layers across the flowing suspension in the test cell at t~300-minutes in the experiment. As the figure indicates, although the colloidal particles have a density (~1.05 g/cm$^3$) close to the carrier fluid (~1 g/cm$^3$), they are still affected by gravitational settling; the profile is biased towards the bottom surface of the horizontal test cell. From this profile, the average concentration of mobile colloids in the bulk suspension can be estimated by dividing the sum of all the mobile colloids found in different layers by the volume of the solution containing these layers. In this particular example, the sum of mobile colloids across the cell's aperture was ~3673 and the volume of the solution containing the particle layers $=(8.1378 \times 10^{-4}$ cm$^2) \times 0.02$ cm≈1.63×10⁻⁵ cm³. Therefore, the bulk concentration of the mobile colloids in the test cell is ≈2.26×10⁸ cm⁻³, about 12.85% higher than the prepared value of 2×10⁸ cm⁻³.

Figure 18:
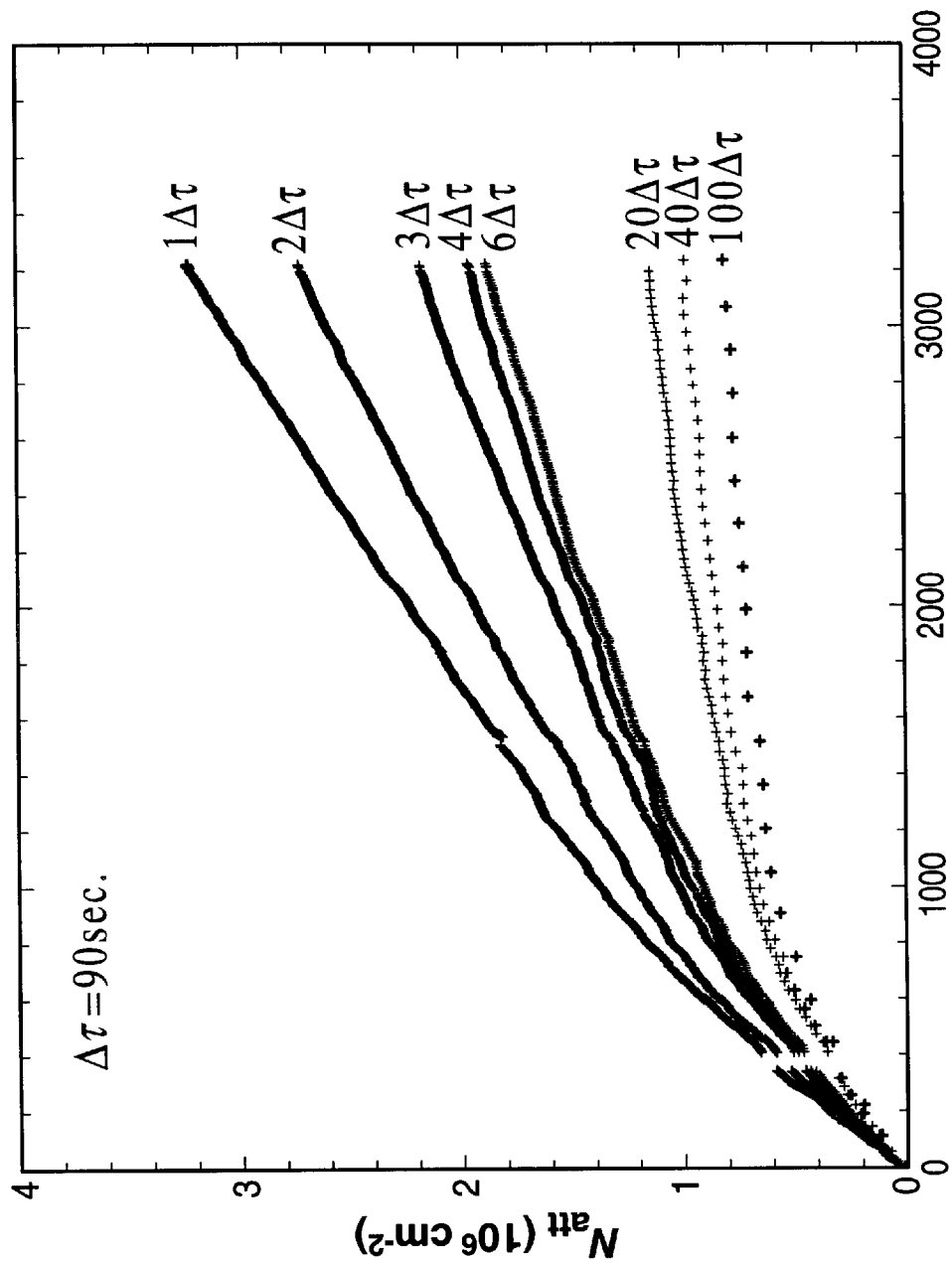
FIG. 18 is a graph of experimental results showing the effect of the time interval between images, $\Delta\tau$, on the obtained value of $N_{att}$.
Figure 19:
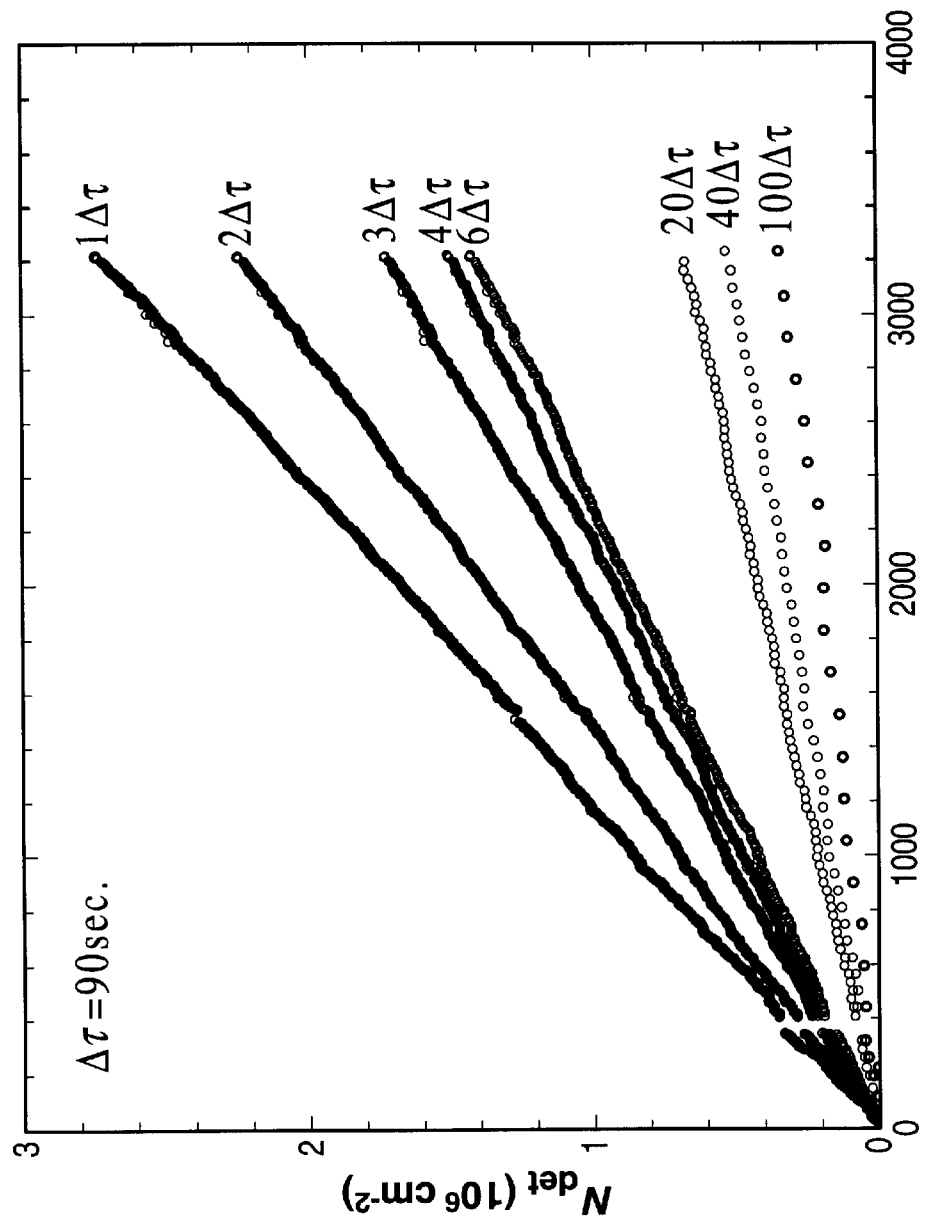
FIG. 19 is a graph of experimental results showing the effect of the time interval between images, $\Delta\tau$, on the obtained value of $N_{det}$.
Figure 20:
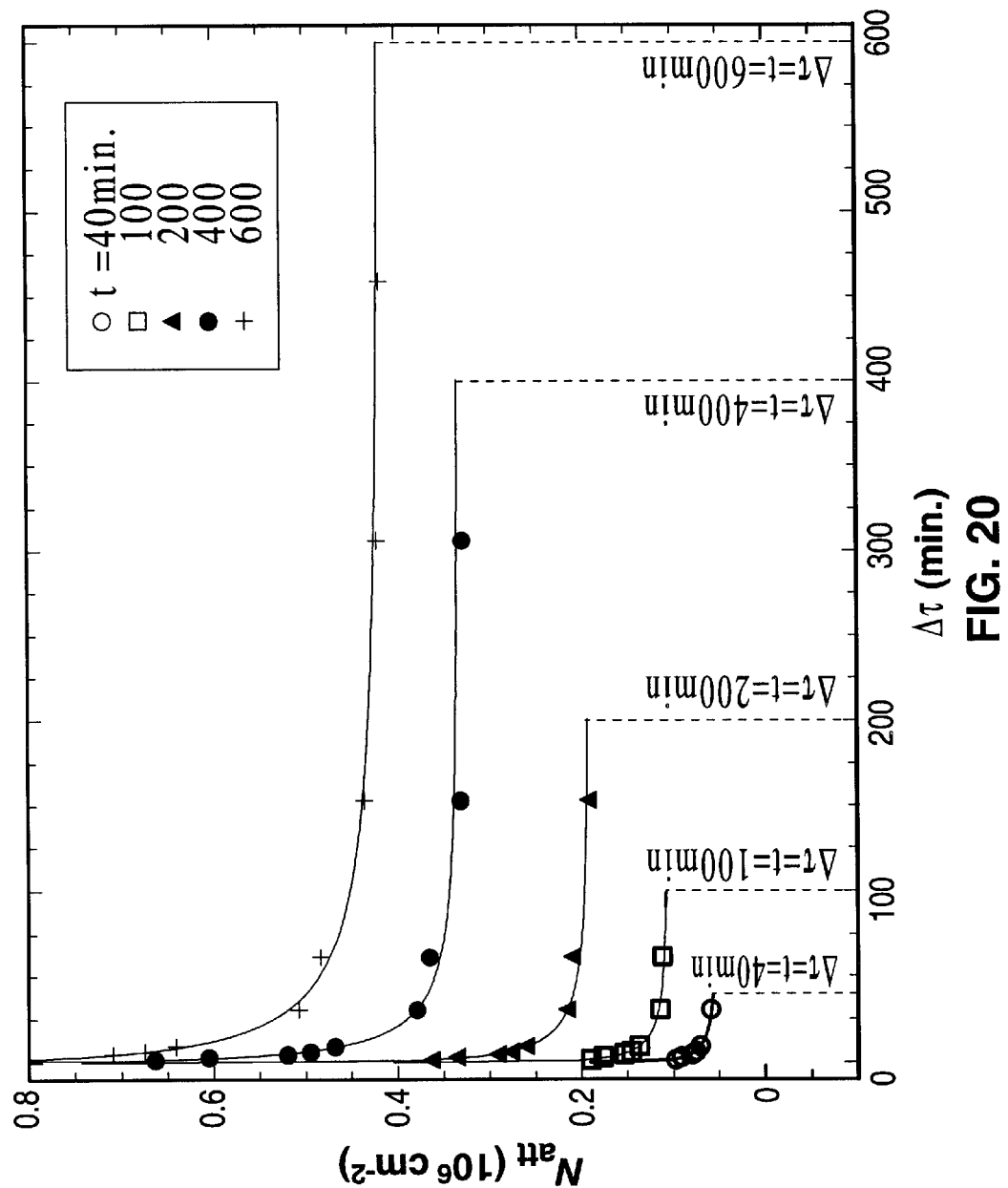
FIG. 20 is a graph of experimental results showing the relation between $N_{att}$ and $\Delta\tau$ at selected times.
Figure 21:
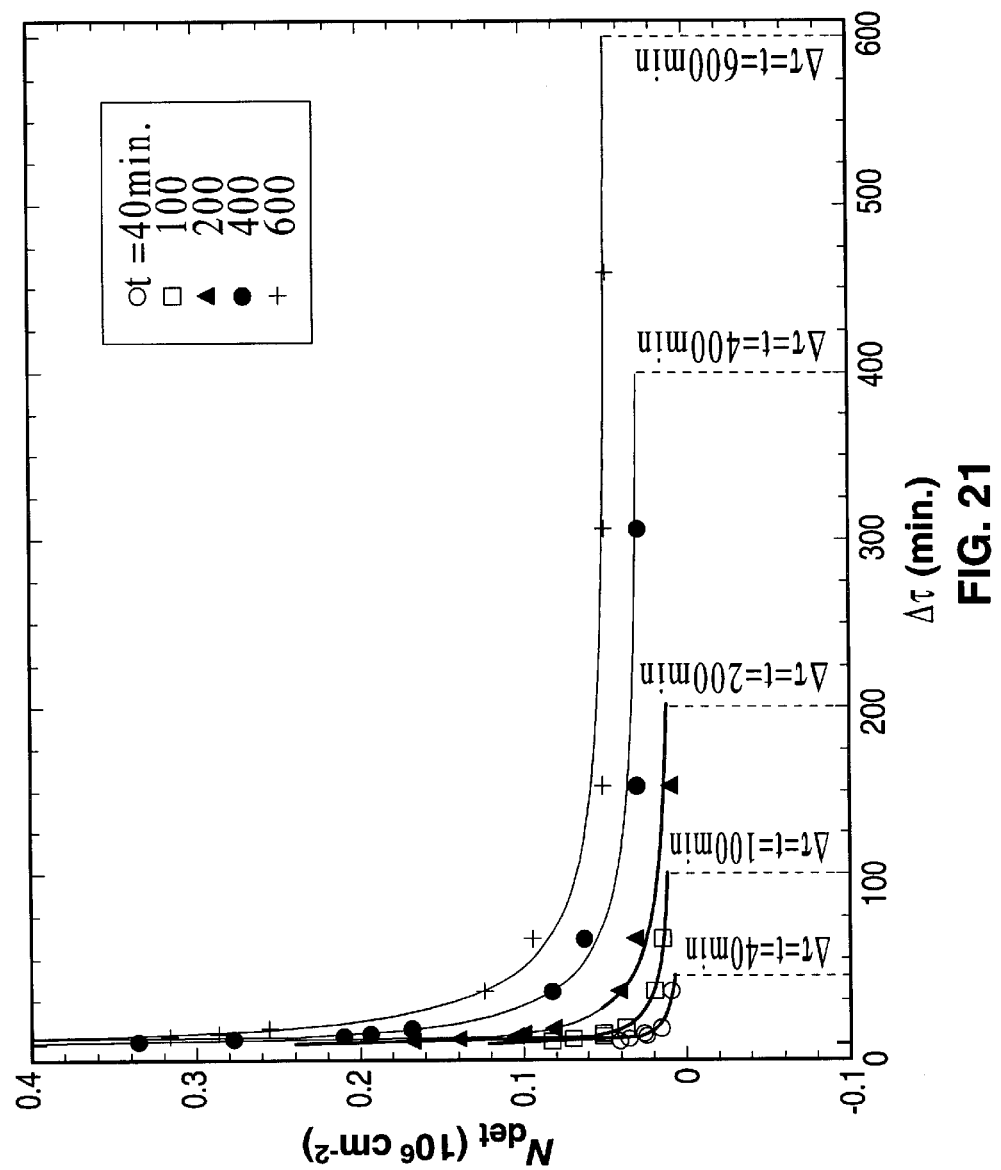
FIG. 21 is a graph showing estimated surface concentration of arriving, departing, and residing particles.
Figure 22:
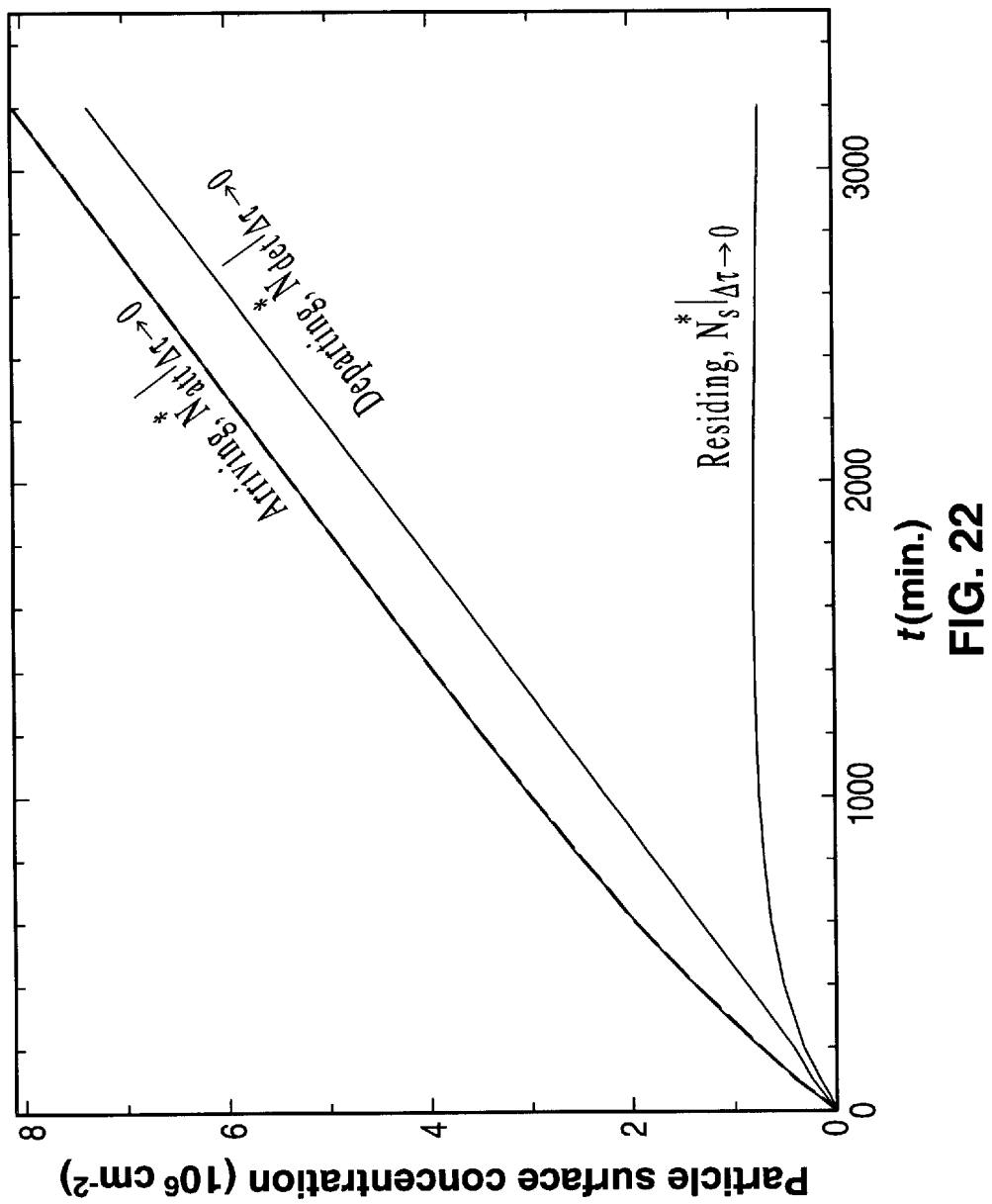
FIG. 22 is a graph showing estimated flux of arriving, departing, and residing particles.

(c) Surface Concentration and Flux of Residing, Arriving, and Departing Particles The changes of $N_{att}$ and $N_{det}$ with time generated by Subroutine 104 assuming different values of $\Delta\tau$ are delineated in FIG. 18 and FIG. 19, respectively. Obviously, the values of $N_{att}$ and $N_{det}$ decrease with increasing $\Delta\tau$, indicating that a larger number of the attachment and detachment events at the surface are missed as $\Delta\tau$ increases. The values of $N_{att}$ and $N_{det}$ at t=40, 100, 200, 400, and 600 minutes for different $\Delta\tau$'s are extracted from each curve in FIG. 18 and FIG. 19. FIG. 20 and FIG. 21, respectively, plot the extracted values of $N_{att}$ and $N_{det}$ versus $\Delta\tau$ at different times. The data points in FIG. 20 and FIG. 21, respectively, are fitted using the expressions:

$$N_{att}(\Delta\tau)|_t = N_{att}(\Delta\tau \to t) + [N^*_{att} - N_{att}(\Delta\tau \to t)]\exp\left(-\frac{\Delta\tau}{T_1}\right)^{1/3}, \text{ and} \quad (28)$$

$$N_{det}(\Delta\tau)|_t = N_{det}(\Delta\tau \to t) + [N^*_{det} - N_{det}(\Delta\tau \to t)]\exp\left(-\frac{\Delta\tau}{T_2}\right)^{1/3}, \quad (29)$$

where $T_1$ and $T_2$ are relaxation times, $N^*_{att}=N_{att}(\Delta\tau=0)$, and $N^*_{det}=N_{det}(\Delta\tau=0)$. Referring also to FIG. 22, from the data fit, the values of $N^*_{att}$, $N^*_{det}$, and $N^*_s$ (the difference between $N^*_{att}$ and $N^*_{det}$), are obtained at different times, t. The corresponding colloid fluxes are calculated from Equations (21), (22), and (24) and plotted in FIG. 23.

Accordingly, the present invention comprises a fully automated video microscopic system for detailed analysis of the deposition of colloids from an aqueous suspension in parallel-plate channels. Detailed quantification of the attachment and detachment of the colloids during their deposition onto the channel's glass surfaces is achieved. On real-time basis, image processing and data extraction and manipulation routines determine: the surface concentration and flux of deposited, attached, and detached colloids for a specific image capturing rate as well as the concentration distribution of mobile colloids in the bulk suspension. From a sequence of saved images, the routines perform extensive data manipulation to determine the actual surface concentration and flux of deposited, attached, and detached particles, i.e., as the time interval between images approaches zero.

The system utilizes dark-field light microscopy and optimizes the tradeoffs between image contrast and resolution and between the field and depth of view. Although it uses standard light as the illumination source, its optical resolution is two times higher than that achieved using a laser beam. Because the system uses standard light as its illumination source, it doesn't require frequent shutting down, thus provides continuous visualization besides minimizing the thermal and radiation pressure effects that can be induced by lasers. This feature suits the system to studying arbitrary particle types including biological cells.

Relatively high contrast images of in focus colloids (≧~300 nm in diameter) on the surface or in the bulk suspension could be obtained. Over 10,000 images can be automatically captured, processed, and analyzed during the course of a typical experiment, improving the experimental statistics and accuracy. The system provides a depth of field that is several times larger than what has been reported for similar systems. Thus, materials with slightly rough surfaces (e.g., thin sections of natural rocks or metals) as well as gas/liquid interfaces can be employed as the deposition surface. The system's wide field of view is more than two times larger than the largest field of view for conventional similar systems. This wide field of view allows more particles to be considered in the analysis, improving the experimental statistics. By automating data acquisition and analysis, the routines makes the extraction of the information required for full quantification of colloid deposition processes over extended periods of time fast, precise, and less subject to human error. Because data are extracted and graphically displayed in real time during the experiments, setup errors, such as a lens being out of focus, can be detected and corrected immediately. In typical laboratory scenarios, in which data are collected over days and analyzed later, such errors can invalidate an entire experiment and result in costly reruns. Connectivity is fully established over time periods on the order of days, reducing errors resulting from the lack of connectivity between successive images.

The automated video-microscopic system of the present invention is a simpler, cheaper, faster, and more precise way to determine colloidal deposition and aggregation kinetics. The invention combines complex, multidisciplinary tasks in one user-friendly tool that is both automated and interactive. It not only reduces human error in data collection and analysis but can be operated by technicians who do not have extensive knowledge of particle physics. Human error and manpower requirements both prove costly in today's conventional approaches to quantifying colloidal deposition kinetics. Finally, the invention offers precision; it measures the volumetric concentrations of colloids with ~6% accuracy.

The invention also has broad market potential. As an automated tool for monitoring protein crystal growth, it could impact the $100 million market for x-ray crystallography. It also has promise in the pharmaceutical industry in the production of active ingredients for clinical animal trials. Utilities in the nuclear power industry could use the invention to help them design more-efficient filters for removing nanoparticles from reactor coolant streams. The invention also has promise for investigating colloidal kinetics as it relates to mining operations, environmental remediation, and materials science. In short, it is a versatile tool for studying a tiny but ubiquitous entity: colloids.

By combining inexpensive hardware with innovative software, the present invention is a versatile, interactive tool for capturing and analyzing particle motion. It reduces not only the manpower required for kinetics experiments but also the potential for human error to invalidate them. And, by solving discrepancies that have perennially plagued efforts to quantify particle attachment and detachment events over long periods of time, it improves the validity of experimental results.

The present invention offers major innovative advances over conventional direct microscopic visualization systems for studying colloidal phenomena. It significantly enhances the measurement of colloidal deposition kinetics by reducing common artifacts in each system component, from optics to image processing to data handling and extraction. The system also applies new, sophisticated methodologies to extract data from an enormous number of images over long periods of time. Yet as a simple, versatile, and highly automated system, it can be operated by non-technical users (i.e., users without advanced physics backgrounds). Other system advances include the following:

1. The particle arrival and deposition concentrations obtained are independent of the experiment design. This provides unique and consistent data that can be compared with other experimental results and with theoretical predictions.

2. Without refocusing, the invention captures both particles immobilized at the surface and those moving close to it, and distinguishes between them. This capability provides a valuable link between surface and subsurface concentrations of particles.

3. Particle concentration, diffusion coefficient, and velocity across the test cell are obtained during deposition or aggregation experiments. These quantities provide the overall kinetics picture of the deposition and aggregation processes and are essential for quantifying particle transport.

4. The invention captures, processes, and analyzes over 10,000 images during the course of a typical experiment, improving experimental statistics and accuracy.

5. Users can interact with the system remotely through the Internet and can share real-time data with others during the course of an experiment.

6. The key data are extracted and displayed on-line, enabling users to quickly identify and correct any experimental setup errors.

7. Connectivity is established over time periods on the order of days, reducing significant errors that result when connectivity is lacking.

8. The invention uses standard light as its illumination source, which eliminates the thermal effects that can be induced by lasers, reduces equipment and operating costs, and suits the system to biological studies.

9. The invention's wide field of view improves experimental statistics.

10. Various materials can be used as the substrate for particle deposition (e.g., thin sections of natural rocks or metals as well as gas/liquid interfaces).

11. Particles at varied depths in a suspension are visualized without deterioration and hence analyzed and quantified with the same accuracy as surface particles.

As a result, the present invention can be used to study cells in their natural environment. The invention determines particle number concentration in the bulk suspension and can in principle measure zeta potential more easily and accurately than commercial instruments that are more than twice as expensive and much less versatile (i.e., measure only one parameter, such as zeta potential).

The present invention is ideal for basic and applied research aimed at detailed quantification of colloid deposition onto varied surfaces. For typical environmental applications, it is directly applicable to studies of the colloidal transport of contaminants in groundwater systems and the effectiveness of filtration systems for drinking and wastewater. Industries involved in paper making, surface cleaning, water-soluble glues, emulsion paints, food and cosmetics, and agriculture can utilize this system. In studies related to micro-contamination, the manufacture of electroluminescent panels and microelectronics, and structure formation and patterning on surfaces, the system can also be of potential use. In pharmaceutical research, the system could automate the analysis of protein crystal growth and the detection of the early onset of protein crystal formation, reducing the costly manpower and human errors commonly encountered in such studies. In medical research, the system could also be applied to study: (1) diseases caused by colloidal transport and deposition, such as cardiac infarctions, strokes, and metastases (due to malignant cells released from a primary tumor); (2) deposition of microorganisms on surgical instruments and implants; (3) microbial adhesion to teeth, such as the formation of plaque; and (4) thrombus formation in vascular prostheses. The system could also be employed in studies of the sorption of colloidal minerals onto a gas-liquid interface, necessary to design effective froth flotation processes that are commonly used to separate gold and other valuable minerals from waste rock.

Finally, the system can be used for accurate particle counting in two ways: (1) by counting the number of particles in different layers across a suspension, which can be done simultaneously while performing a deposition experiment (with ~12% accuracy), or (2) by using a solution chemistry that allows fast deposition of particles onto the surfaces of the test cell and then counting them at those surfaces (with ~5% accuracy).

Many other industries are also interested in colloidal deposition kinetics, including those involved in paper making, surface cleaning, water-soluble glues, emulsion paints, food and cosmetics, and agriculture.

Those skilled in the art will appreciate that other devices and subsystems could be included, and that the devices and subsystems shown may be interconnected in different ways than shown in the embodiment described herein. It will further be appreciated that not all of the devices shown are necessary to practice the present invention, and that the present invention may be implemented on any conventional computer system under processor control. Additionally it will be appreciated that the software code to implement the invention as described herein can be written for various platforms using conventional programming techniques, and that the software could be stored on any convenient media that can be accessed by the computer.

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Truth table for the logical "AND" and "OR" operations.

| Pixel 1 | Pixel 2 | Pixel 1 AND Pixel 2 | Pixel 1 OR Pixel 2 |
| --- | --- | --- | --- |
| 0 | 0 | 0 | 0 |
| 0 | 1 | 0 | 1 |
| 1 | 0 | 0 | 1 |
| 1 | 1 | 1 | 1 |

TABLE 2

Figure 9:
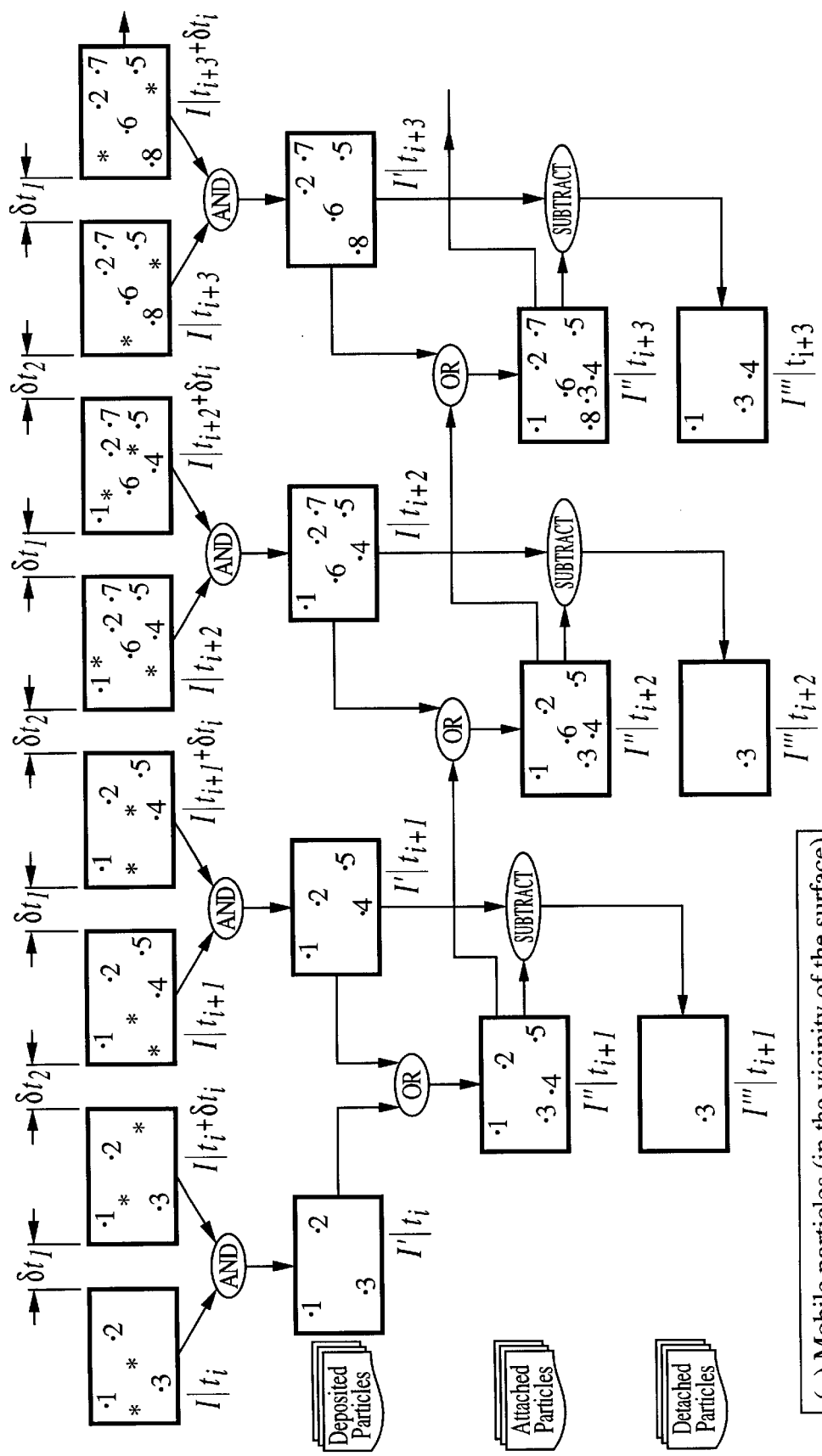
FIG. 9 is a flow and logic diagram showing a method for identifying the deposited, attached and detached colloids at the surface of a parallel-plate test cell according to the present invention.

Counts from FIG. 9 (without connectivity) and FIG. 10 (with connectivity).

| Binary Operation | Particle Counts | | |
|---|---|---|---|
| | Correct | Without connectivity established (FIG. 11) | With connectivity established (FIG. 12) |
| $I_1$ OR $I_2$ | 8 | 16 | 8 |
| $I_1$ AND $I_2$ | 8 | 0 | 8 |
| $I_1 - I_2$ | 0 | 8 | 0 |

What is claimed is:

1. A video-microscopic imaging and data acquisition apparatus for colloid deposition measurements, comprising:
   (a) an optical microscope;
   (b) a digital imaging device coupled to said microscope;
   (c) a computer coupled to said digital imaging device; and
   (d) means associated with said computer for visualizing and characterizing colloidal particles that are suspended in or at the surface of a parallel-plate test cell imaged by said optical microscope.

2. An apparatus as recited in claim 1, wherein said visualization and characterization comprises determining the cumulative concentration of colloidal particles attaching to and detaching from surface of the test cell.

3. An apparatus as recited in claim 1, wherein said visualization and characterization comprises determining the evolution of mobile and immobile colloidal particles at the surface of the test cell.

4. An apparatus as recited in claim 1, wherein said visualization and characterization comprises determining the concentration profile of colloidal particles across the bulk suspension in the test cell.

5. An apparatus as recited in claim 1, wherein said imaging device comprises a high-resolution black-and-white CCD camera.

6. An apparatus as recited in claim 1:
   further comprising a high resolution black-and-white video monitor coupled to said imaging device;
   wherein said monitor is configured for displaying images from said digital imaging device; and
   wherein said visualizing and characterizing means is configured for displaying real time visualizing and characterizing results on said monitor.

7. An apparatus as recited in claim 1, wherein dark-field illumination is employed to visualize the colloids at a substrate comprising either the bottom or the top inner surface of the test cell and in the bulk suspension.

8. An apparatus as recited in claim 1, wherein said test cell comprises a parallel-plate flow cell having inlet ports and outlet ports and a sealed channel between said inlet and outlet ports.

9. An apparatus as recited in claim 1, further comprising means for displaying colloidal particles as bright specks against a dark background.

10. An apparatus as recited in claim 1, wherein data is extracted and displayed for said colloidal particles in real time.

11. A video-microscopic imaging and data acquisition apparatus for colloid deposition measurements, comprising:
    (a) an optical microscope;
    (b) a digital imaging device coupled to said microscope;
    (c) a computer coupled to said digital imaging device; and
    (d) means associated with said computer for determining in real time at least one characteristic of colloidal particles that are suspended in or at the surface of the test cell selected from the group of characteristics consisting of:
       (i) the cumulative concentration of colloidal particles attaching to and detaching from surface of the test cell,
       (ii) the evolution of mobile and immobile colloidal particles at the surface of the test cell, and
       (iii) the concentration profile of colloidal particles across the bulk suspension in the test cell.

12. An apparatus as recited in claim 11, wherein said imaging device comprises a high-resolution black-and-white CCD camera.

13. An apparatus as recited in claim 11:
    further comprising a high resolution black-and-white video monitor coupled to said imaging device;
    wherein said monitor is configured for displaying images from said digital imaging device and displaying real time visualizing and characterizing results.

14. An apparatus as recited in claim 11, wherein dark-field illumination is employed to visualize the colloids at a substrate comprising either the bottom or the top inner surface of the test cell and in the bulk suspension.

15. An apparatus as recited in claim 11, wherein said test cell comprises a parallel-plate flow cell having inlet ports and outlet ports and a sealed channel between said inlet and outlet ports.

16. An apparatus as recited in claim 11, further comprising means for displaying colloidal particles as bright specks against a dark background.

17. An apparatus as recited in claim 16, wherein data is extracted and displayed for said colloidal particles in real time.

18. A video microscopic imaging and data acquisition apparatus for colloid deposition visualization and characterization, comprising:
    (a) an optical microscope configured for performing dark-field microscopy;
    (b) a digital imaging device coupled to said microscope;
    (c) a computer coupled to said digital imaging device; and
    (d) programming associated with said computer for carrying an out an operation selected from the group of operations consisting of
       (i) determining the cumulative concentration of colloidal particles attaching to and detaching from surface of a parallel-plate test cell in the field of view of the microscope,
       (ii) determining the evolution of mobile and immobile colloidal particles at the surface of a parallel-plate test cell in the field of view of the microscope, and
       (iii) determining the concentration profile of colloidal particles across the bulk suspension in a parallel-plate test cell in the field of view of the microscope.

19. An apparatus as recited in claim 18, wherein said imaging device comprises a high-resolution black-and-white CCD camera.

20. An apparatus as recited in claim 18:
    further comprising a high resolution black-and-white video monitor coupled to said imaging device;
    wherein said video monitor is configured for displaying images from said digital imaging device and displaying real time visualizing and characterizing results.

21. An apparatus as recited in claim 18, wherein dark-field illumination is employed to visualize the colloids at a substrate comprising either the bottom or the top inner surface of the test cell and in the bulk suspension.

22. An apparatus as recited in claim 18, wherein said test cell comprises a parallel-plate flow cell having inlet ports and outlet ports and a sealed channel between said inlet and outlet ports.

23. An apparatus as recited in claim 18, further comprising means for displaying colloidal particles as bright specks against a dark background.

24. An apparatus as recited in claim 23, wherein data is extracted and displayed for said colloidal particles in real time.

25. A method for imaging colloid deposition in a parallel plate test cell, comprising:
   (a) positioning a parallel-plate test cell in the field of view of an optical microscope coupled to a digital imaging device and a computer;
   (b) illuminating said parallel-plate test cell with dark-field illumination; and
   (c) determining a characteristic of colloidal particles that are suspended in or at the surface of the test cell selected from the group of characteristics consisting of:
      (i) the cumulative concentration of colloidal particles attaching to and detaching from surface of the test cell,
      (ii) the evolution of mobile and immobile colloidal particles at the surface of the test cell, and
      (iii) the concentration profile of colloidal particles across the bulk suspension in the test cell.

26. A method as recited in claim 25, wherein said imaging device comprises a high-resolution black-and-white CCD camera.

27. A method as recited in claim 25, further comprising employing dark-field illumination to image the colloids at a substrate comprising either the bottom or the top inner surface of the test cell and in the bulk suspension.

28. A method as recited in claim 25, wherein said test cell comprises a parallel-plate flow cell having inlet ports and outlet ports and a sealed channel between said inlet and outlet ports.

29. A method as recited in claim 25, further displaying colloidal particles as bright specks against a dark background.

30. A method as recited in claim 29, further comprising displaying data extracted for said colloidal particles in real time.

31. A video-microscopic imaging and data acquisition computer program for measuring and extracting colloid deposition in real time in or at the surface of a parallel-plate test cell imaged by an optical microscope, comprising a set of instructions stored on media accessible by a computer and executable on said computer for carrying out an operation selected from the group of operations consisting of
   (i) determining the cumulative concentration of colloidal particles attaching to and detaching from surface of a parallel-plate test cell in the field of view of the microscope,
   (ii) determining the evolution of mobile and immobile colloidal particles at the surface of a parallel-plate test cell in the field of view of the microscope, and
   (iii) determining the concentration profile of colloidal particles across the bulk suspension in a parallel-plate test cell in the field of view of the microscope.

32. An apparatus as recited in claim 1:
   further comprising an illumination source directed to colloidal particles imaged by said optical microscope;
   wherein said illumination source comprises a standard, non-laser, light source.

33. An apparatus as recited in claim 1, wherein said means for visualizing and characterizing is configured for performing AND, OR, or SUBTRACT operations on sequential images and superimposing the results on said imaging device.

34. An apparatus as recited in claim 7, wherein said substrate can comprise transparent or opaque material.

35. An apparatus as recited in claim 8, wherein said test cell need not incorporate an optical prism, and does not require dying the colloids with a fluorescent dye.

36. An apparatus as recited in claim 11:
   further comprising an illumination source directed to colloidal particles imaged by said optical microscope;
   wherein said illumination source comprises a standard, non-laser, light source.

37. An apparatus as recited in claim 13, wherein said means associated with said computer for determining the characteristic of colloidal particles is configured for superimposing sequential images for output on said video monitor.

38. An apparatus as recited in claim 37, wherein a mathematical or logical operation is performed on sequential images being superimposed.

39. An apparatus as recited in claim 38, wherein said logical or mathematical operation comprises AND, OR, or SUBTRACT operations.

40. An apparatus as recited in claim 14, wherein said substrate can comprise transparent or opaque material.

41. An apparatus as recited in claim 15, wherein said test cell need not incorporate an optical prism, and does not require dying the colloids with a fluorescent dye.

42. An apparatus as recited in claim 18:
   further comprising an illumination source directed to colloidal particles imaged by said optical microscope;
   wherein said illumination source comprises a standard, non-laser, light source.

43. An apparatus as recited in claim 18, wherein said programming is further configured for superimposing sequential images on said digital imaging device.

44. An apparatus as recited in claim 43, wherein a mathematical or logical operation is performed on sequential images to be superimposed.

45. An apparatus as recited in claim 44, wherein said logical or mathematical operation comprises AND, OR, or SUBTRACT operations.

46. An apparatus as recited in claim 21, wherein said substrate can comprise transparent or opaque material.

47. An apparatus as recited in claim 22, wherein said test cell need not incorporate an optical prism, and does not require dying the colloids with a fluorescent dye.

48. A method as recited in claim 25, wherein said illuminating can be performed utilizing a standard, non-laser, light source.

49. A method as recited in claim 25, wherein said determining the characteristics of colloidal particles further comprises superimposing sequential images.

50. A method as recited in claim 49, wherein said superimposing is based on AND, OR, or SUBTRACT operations performed on sequential images.

51. A method as recited in claim 27, wherein said substrate can comprise a transparent or opaque material.

52. A method as recited in claim 28, wherein said test cell need not incorporate an optical prism, and does not require dying the colloids with a fluorescent dye.

* * * * *